(12) United States Patent
Valmier et al.

(10) Patent No.: US 10,065,937 B2
(45) Date of Patent: Sep. 4, 2018

(54) FLT3 RECEPTOR ANTAGONISTS

(71) Applicants: INSERM (INSTITUT NATIONAL DE LA SANTÉ ET DE LA RECHERCHE MÉDICALE), Paris (FR); UNIVERSITE DE MONTPELLIER, Montpellier (FR); CENTRE NATIONAL DE LA RECHERCHE SCIENTIFIQUE (CNRS), Paris (FR); UNIVERSITÉ DE STRASBOURG, Strasbourg (FR)

(72) Inventors: Jean Valmier, Montpellier (FR); Jean-Philippe Leyris, Montpellier (FR); Didier Rognan, Illkirch (FR); Martine Schmitt, Illkirch (FR)

(73) Assignees: INSERM (INSTITUT NATIONAL DE LA SANTE ET DE LA RECHERCHE MEDICALE), Paris (FR); UNIVERSITE DE MONTPELLIER, Montpellier (FR); CENTRE NATIONAL DE LA RECHERCHE SCIENTIFIQUE (CNRS), Paris (FR); UNIVERSITE DE STRASBOURG, Strasbourg (FR)

( * ) Notice: Subject to any disclaimer, the term of this patent is extended or adjusted under 35 U.S.C. 154(b) by 0 days.

(21) Appl. No.: 15/500,174

(22) PCT Filed: Jul. 30, 2015

(86) PCT No.: PCT/EP2015/067510
§ 371 (c)(1),
(2) Date: Jan. 30, 2017

(87) PCT Pub. No.: WO2016/016370
PCT Pub. Date: Feb. 4, 2016

(65) Prior Publication Data
US 2017/0233354 A1    Aug. 17, 2017

(30) Foreign Application Priority Data

Jul. 31, 2014 (EP) .................................. 14306225

(51) Int. Cl.
| | | |
|---|---|---|
| *C07D 295/26* | (2006.01) | |
| *C07D 209/08* | (2006.01) | |
| *C07D 249/08* | (2006.01) | |
| *C07D 233/64* | (2006.01) | |
| *C07D 235/04* | (2006.01) | |
| *C07D 257/04* | (2006.01) | |
| *C07C 311/20* | (2006.01) | |
| *A61K 31/4453* | (2006.01) | |
| *A61K 31/454* | (2006.01) | |
| *A61K 31/18* | (2006.01) | |

(52) U.S. Cl.
CPC ............ *C07D 295/26* (2013.01); *A61K 31/18* (2013.01); *A61K 31/4453* (2013.01); *A61K 31/454* (2013.01); *C07C 311/20* (2013.01); *C07D 209/08* (2013.01); *C07D 233/64* (2013.01); *C07D 235/04* (2013.01); *C07D 249/08* (2013.01); *C07D 257/04* (2013.01)

(58) Field of Classification Search
CPC .. A61K 31/18; A61K 31/4453; A61K 31/454; C07C 311/20; C07D 209/08; C07D 233/64; C07D 235/04; C07D 249/08; C07D 257/04; C07D 295/26
See application file for complete search history.

(56) References Cited

U.S. PATENT DOCUMENTS

2014/0163017 A1*  6/2014  Vankayalapati ...... C07C 311/16
                                                           514/227.5

FOREIGN PATENT DOCUMENTS

| EP | 2280001 A1 | 2/2011 |
|---|---|---|
| WO | 2009/061446 A1 | 5/2009 |
| WO | 2009/095399 A2 | 8/2009 |
| WO | 2010/123139 A1 | 10/2010 |

OTHER PUBLICATIONS

Fells, et al., Targeting the hydrophobic pocket of autotaxin with virtual screening of inhibitors identifies a common aromatic sulfonamide structural motif, FEBS Journal, 281(4), 1017-1028 (2014).*
Bychenkov, et al., Method for preparation of sulfonamide derivatives of dibenzo[b,f][1,4]oxazepin-11(10H)-one from 3-sulfo-5-chlorobenzoic acid dichloride, Izvestiya Vysshikh Uchebnykh Zavedenii, Khimiya i Khimicheskaya Tekhnologiya, 51(4), 5-6 (2008).*
Lambeng et al: "Arylusulfonamides as a new class of cannabinoid CB1 receptor ligands: Identification of a lead and initial SAR studies", Bioorganic & Medicinal Chemistry Letters, Pergamon, Amsterdam, NL, vol. 17, No. 1, pp. 272-277, Dec. 22, 2006.
Database Pubchem Compounds [Online] NCBI, CID 1262923, Jul. 10, 2005.

* cited by examiner

*Primary Examiner* — Erich A Leeser
(74) *Attorney, Agent, or Firm* — Whitham & Cook, P.C.

(57) ABSTRACT

The invention pertains to novel FLT3 receptor antagonists of general formula (1). The compounds are useful for the treatment or the prevention of pain disorders, cancer and autoimmune diseases.

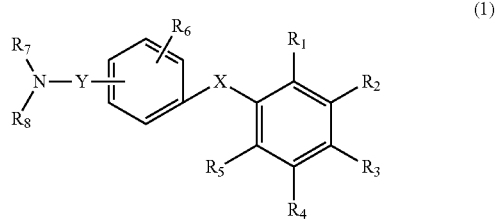

(1)

16 Claims, No Drawings

FLT3 RECEPTOR ANTAGONISTS

FIELD OF THE INVENTION

The present invention relates to FLT3 receptor antagonists for the treatment or the prevention of pain disorders, cancer and autoimmune diseases.

BACKGROUND OF THE INVENTION

Somatic sensations such as warming, cooling, gentle touch and pain are each initiated by activation of sensory neurons. Specific types of sensory neurons, whose cell bodies are located in dorsal root and trigeminal ganglia, subserve different sensory modalities. Specialized sensory neurons called nociceptors are responsible for the transduction of painful thermal and mechanical stimulation of the skin. Knowledge about molecules and ion channels that are necessary for the normal transduction of painful thermal and mechanical stimuli is still incomplete. It has been postulated that thermosensitive ion channels of the TRP family are important for the transduction of noxious heat or cold by nociceptive sensory neurons (Jordt et al., 2003). The most complete evidence exists for the capsaicin activated ion channel TRPV1 that can be activated by thermal stimuli in the noxious range. Mice lacking TRPV1 have altered pain behavior and do not respond to the noxious irritant capsaicin. An important feature of pain is the fact that injury and inflammation leads to heightened sensitivity to stimuli that would normally be only mildly painful. This phenomenon is called hyperalgesia, and the prevention of hyperalgesia is a hallmark of effective analgesia. TRPV1 may become an important analgesic target because this channel is required for the expression of thermal hyperalgesia provoked by inflammation (Caterina et al., 2000; Davis et al., 2000).

Moreover, molecules up-regulated in inflamed tissue such as nerve growth factor (NGF) can sensitize peripheral nociceptors to thermal stimuli. NGF signaling via its receptor tyrosine kinase TrkA constitutes a physiological mediator of inflammatory hyperalgesia. It has been known for many years that the dorsal root ganglion (DRG) neurons that require NGF are all nociceptors. NGF can produce a profound and long lasting thermal and mechanical hyperalgesia in man and animals. NGF can also potentiate TRPV1 mediated and noxious heat activated ionic currents in isolated DRG neurons. Indeed, NGF injected into animals produces thermal hyperalgesia that requires the presence of TRPV1 (Chuang et al., 2001).

Around half of the nociceptors in the adult DRG possess TrkA receptors; the remainder, defined by the expression of c-Ret, downregulate TrkA during early postnatal development. The receptor tyrosine kinase c-Ret mediates signals elicited by the glial-derived neurotophic factor (GDNF) ligand family. The c-Ret receptor and its co-receptors GFRα2 and 3 are present in nociceptive neurons, some of which are heat sensitive and express TRPV1 receptors. Indeed, there is some evidence for a role of the GDNF family ligands neurturin and artemin in regulating noxious heat transduction by sensory neurons (Malin et al., 2006).

In addition to the Trk and c-Ret receptors, sensory neurons are known to express other receptor tyrosine kinases like c-Kit, the receptor for stem cell factor (SCF). Thus, the European patent application No EP 2 068 152 discloses that the central role for SCF and its receptor, c-Kit, in tuning the responsiveness of sensory neurons to natural stimuli and that c-Kit can now be grouped with a small family of receptor tyrosine kinases, including c-Ret and TrkA, that control the transduction properties of sensory neurons. Said patent application claims the use of a c-kit receptor antagonist such as the small molecule drug imatinib for treating or preventing a disorder selected from pain, hyperalgesia and inflammatory pain.

WO2011/083124 (Valmier et al) provides for the first time evidence that that FL, via its specific interaction with FLT3, plays a critical role in modulating noxious thermal and mechanical pain sensitivity in vivo and suggests FLT" receptor antagonists for the treatment and the prevention of pain.

FLT3 receptor antagonists arte known and described in a number of publications and patent applications, e.g. Sternberg et al. 2004 and WO 2002032861, WO 2002092599, WO 2003035009, WO 2003024931, WO 2003037347, WO 2003057690, WO 2003099771, WO 2004005281, WO 2004016597, WO 2004018419, WO 2004039782, WO 2004043389, WO 2004046120, WO 2004058749, WO 2004058749, WO 2003024969, WO 2006/138155, WO 2007/048088 and WO 2009/095399.

FLT3 receptor antagonists may consist in FLT3 kinase inhibitors. Examples of FLT3 kinase inhibitors include AG1295 and AG1296; Lestaurtinib (also known as CEP-701, formerly KT-5555, Kyowa Hakko, licensed to Cephalon); CEP-5214 and CEP-7055 (Cephalon); CHIR-258 (Chiron Corp.); GTP 14564 (Merck Biosciences UK). Midostaurin (also known as PKC 412 Novartis AG); MLN-608 (Millennium USA); MLN-518 (formerly CT53518, COR Therapeutics Inc., licensed to Millennium Pharmaceuticals Inc.); MLN-608 (Millennium Pharmaceuticals Inc.); SU-11248 (Pfizer USA); SU-11657 (Pfizer USA); SU-5416 and SU-5614; THRX-165724 (Theravance Inc.); AMI-10706 (Theravance Inc.); VX-528 and VX-680 (Vertex Pharmaceuticals USA, licensed to Novartis (Switzerland), Merck & Co USA); and XL 999 (Exelixis USA).

Examples of selective FLT3 receptor antagonists are described in Zarrinkar et al. 2009 and in International Patent Applications No WO 2007/109120 and WO 2009/061446.

SUMMARY OF THE INVENTION

The instant invention provides novel selective FLT3 receptor antagonists with a high potency.

The compounds are of general formula (1):

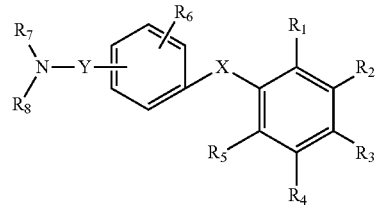

wherein the various substituents are as defined below.

The invention also pertains to compounds of general formula (1) as medicaments. Compounds of general formula (1) are useful for the treatment of pain disorders, in particular chronic pain and neuropathic pain.

Compounds of general formula I are also useful for the treatment of cancer.

Compounds of general formula I are also useful for the treatment of autoimmune diseases.

The invention further pertains to pharmaceutical compositions comprising a novel compound according to the invention.

The invention further pertains to a method for the treatment of pain disorders comprising administering to a subject in need thereof a compound as defined herein.

The invention further pertains to a method for the treatment of cancer comprising administering to a subject in need thereof a compound as defined herein.

The invention further pertains to a method for the treatment of an autoimmune disease comprising administering to a subject in need thereof a compound as defined herein.

DETAILED DESCRIPTION OF THE INVENTION

Definitions

Throughout the specification, several terms are employed and are defined in the following paragraphs.

The terms "FLT3" or "FLT3 receptor" (fms-related tyrosine kinase 3), also known as the CD135, Ly72, Flk-2, Flt-3 or B230315G04, are used interchangeably and have their general meaning in the art. The FLT3 receptor can be from any source, but typically is a mammalian (e.g., human and non-human primate) FLT3 receptor, particularly a human FLT3 receptor.

The terms "FL" or "FLT3-Ligand" are used interchangeably and have their general meaning in the art. They refer to the cytokine which is a natural ligand of the FLT3 receptor. FL can be from any source, but typically is a mammalian (e.g., human and non-human primate) FL, particularly a human FL.

The terms "FLT3 receptor antagonist" includes compounds that, upon administration to a patient, results in inhibition or down-regulation of a biological activity associated with activation of the FLT3 receptor by FL in the patient, including any of the downstream biological effects otherwise resulting from the binding to FLT3 receptor with FL.

In the context of the present invention, FLT3 receptor antagonists are selective for the FLT3 receptor as compared with the other tyrosine kinase receptors, such as c-Kit receptor. By "selective" it is meant that the affinity of the antagonist for the FLT3 receptor is at least 10-fold, preferably 25-fold, more preferably 100-fold, still preferably 150-fold higher than the affinity for the other tyrosine kinase receptors (c-Kit receptor).

As used herein, the term "subject" denotes a mammal, such as a rodent, a feline, a canine, and a primate. Preferably, a subject according to the invention is a human.

In its broadest meaning, the term "treating" or "treatment" refers to reversing, alleviating, inhibiting the progress of, or preventing the disorder or condition to which such term applies, or one or more symptoms of such disorder or condition.

In particular, "prevention" of pain may refer to the administration of the compounds of the present invention prevent the symptoms of pain.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The invention relates to a compound of general formula (1)

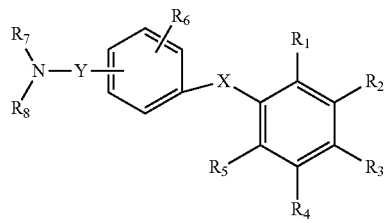

wherein

X is selected from bond, CO, NH, CONH, NHCO, and a 5- or 6-member heteroaromatic group comprising 2 or 3 N atoms;

Y represents $SO_2$ or a bond;

$R_1$, $R_2$, $R_3$, $R_4$ and $R_5$ identical or different are selected from H, OH, alkyl, halo, cyano, trifluoromethyl, alkyloxy, aryl, aryl-alkyl, acyl, COO $R_{11}$, O—$(CH_2)_p$—O-alkyl, 1H-tetrazolyl; $PO_4H_2$, amidino and N-hydroxyamidino;

with the proviso that at least one of $R_1$ to $R_5$ is different from H;

or $R_1$ is as defined above and two from $R_2$ and $R_3$ or $R_3$ and $R_4$ or $R_4$ and $R_5$ together with the carbon atoms to which they are attached form an aromatic ring comprising 5 to 6 members, and the others from $R_2$ to $R_5$ represent H;

or $R_1$ or $R_5$ together with the N or the C atom from X form a heterocyclic aromatic or non aromatic ring comprising 1 or 2 N atoms, and optionally one O atom; and the others from $R_2$ to $R_4$ are as defined above;

$R_6$ is selected from H, halo, hydroxy, alkyl, hydroxyalkyl and alkoxy, or $R_1$ together with $R_6$ form a O or a NH chain, and when Y is $SO_2$, $R_7$ is selected from H, alkyl, cycloalkyl, phenyl, benzyl and $(CH_2)_q$—$R_{12}$, $R_8$ is selected from H, alkyl, cycloalkyl/adamantyl), pyridyl and $(CH_2)_r$—$R_{13}$;

or $R_7$ and $R_8$ together with the N atom to which they are attached form a group of formula:

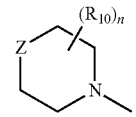

wherein Z is a bond or Z is selected from $CHR_{14}$, $CH_2CHR_{14}$, $NR_{14}$, $CH_2NR_{14}$ and O, $R_{10}$ is selected from H, alkyl, hydroxyl, halo, trifluoromethyl, aryl; hydroxyalkyl, or two adjacent $R_{10}$ groups together with the cyclic atoms to which they are attached form an aryl group; or when Y is a bond, $R_7$ is H, alkyl, hydroxyalkyl or represents a mono or bicyclic optionally bridged cycloalkyl ring, optionally substituted with one to 3 groups selected from alkyl, arylalkyl and hydroxyalkyl and $R_8$ is $SO_2$ $R_{16}$, $R_{12}$ is selected from OH, COOH, CO-alkyl, phenyl, morpholino, $NH_2$, NH-alkyl, N-(alkyl)$_2$ NH(NH) $NH_2$, and $CH_2COO$-alkyl;

$R_{13}$ is selected from OH, and phenyl;

$R_{14}$ is selected from H, alkyl, cycloalkyl, aryl, and arylalkyl, wherein the cycloalkyl or aryl ring may comprise one or two heteroatoms in the cyclic structure selected from N and O and may be substituted with one or more substituent selected from alkyl, halo, cyano, amino, alkyl amino, dialkyamino, nitro, trifluoromethyl, aryl, alkyl-aryl, acyl, alkyloxy or aryloxy;

$R_{16}$ represents a group selected from alkyl, hydroxyalkyl, aryl, heteroaryl and arylalkyl;

n is 0, 1, 2 or 3;
p is 0, 1, 2, 3 or 4;
q is 0, 1, 2, 3 or 4;
r is 0, 1, 2, 3 or 4;

Y is in position meta with respect to the X group and $R_6$ is in any position with respect to the X group, or a pharmaceutically acceptable salt thereof, with the exclusion of the following compounds:

N-(2-hydroxy-5-methylphenyl)-3-(piperidine-1-sulfonyl) benzamide;
3-(diethylsulfamoyl)-N-(2-hydroxy-5-methylphenyl)benzamide;
N-(2-hydroxy-5-methylphenyl)-3-(pyrrolidine-1-sulfonyl) benzamide;
N-(5-chloro-2-hydroxyphenyl)-3-(piperidine-1-sulfonyl) benzamide;
N-(2-hydroxyphenyl)-4-methyl-3-(piperidine-1-sulfonyl) benzamide;
2-chloro-N-(2-hydroxyphenyl)-5-(piperidine-1-sulfonyl) benzamide;
N-(2-hydroxyphenyl)-3-(piperidine-1-sulfonyl)benzamide;
N-(5-tert-butyl-2-hydroxyphenyl)-3-(piperidine-1-sulfonyl) benzamide;
N-(2-hydroxy-4-methylphenyl)-3-(piperidine-1-sulfonyl) benzamide;
N-(2-hydroxy-5-methylphenyl)-3-(piperidine-1-sulfonyl) benzamide;
N-(2-hydroxy-5-methylphenyl)-4-methoxy-3-(piperidine-1-sulfonyl)benzamide;
3-(azepane-1-sulfonyl)-N-(2-hydroxy-5-methylphenyl)-4-methoxybenzamide.

The compounds excluded therein are commercially available compounds.

No pharmacological activity is described in connection with these compounds.

More specifically, the invention pertains to compounds of general formula (2)

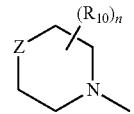

wherein
X is selected from a bond, CO, NH, CONH, NHCO and a 5- or 6-member heteroaromatic group comprising 2 or 3 N atoms;
Y represents $SO_2$ or a bond,
Q is selected from a group of formula:

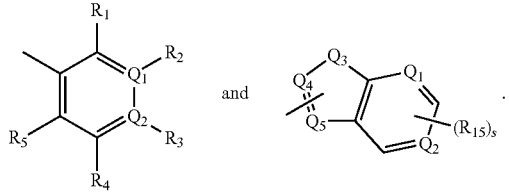

$R_1$ is selected from $OR_{11}$, $COO R_{11}$, halo, 1H-tetrazolyl; $PO_4H_2$, amidino and N-hydroxyamidino;
$R_2$ is selected from H, alkyl, halo, $OR_{11}$ and $COR_{11}$;
$R_3$ is selected from H, $OR_{11}$, halo and O—$(CH_2)_p$—O-alkyl;
$R_4$ is selected from H, alkyl, halo, CO-alkyl ($C_1$-$C_6$), CN, trifluoromethyl, CO-alkyl, phenyl and benzyl;
$R_5$ is H;
or $R_1$ is as defined above and two from $R_2$ and $R_3$ or $R_3$ and $R_4$ or $R_4$ and $R_5$ together with the carbon atoms to which they are attached form an aromatic ring comprising 5 to 6 members, and the others from $R_2$ to $R_5$ represent H;
$R_6$ is selected from H, OH, halo, alkyl, hydroxyalkyl and alkoxy,
or $R_1$ together with $R_6$ form a O or a NH chain;
when Y represents $SO_2$,
$R_7$ is selected from H, alkyl, cycloalkyl, phenyl, benzyl, $(CH_2)_q$—$R_{12}$,
$R_8$ is selected from H, alkyl, cycloalkyl/adamantyl), pyridyl, $(CH_2)_r$—$R_{13}$;
or $R_7$ and $R_8$ together with the N atom to which they are attached form a group of formula:

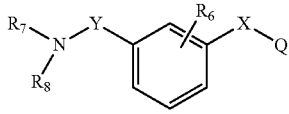

wherein Z is a bond or Z is selected from $CHR_{14}$, $CH_2CHR_{14}$, $NR_{14}$, $CH_2NR_{14}$, and O,
$R_{10}$ is selected from H, alkyl, hydroxyl, halo, trifluoromethyl, aryl and hydroxyalkyl,
or two adjacent $R_{10}$ groups together with the cyclic atoms to which they are attached form an aryl group; and
when Y is a bond,
$R_7$ is H, alkyl, hydroxyalkyl or represents a mono or bicyclic optionally bridged cycloalkyl ring, optionally substituted with one to 3 groups selected from alkyl, arylalkyl and hydroxyalkyl, and
$R_8$ is $SO_2 R_{16}$,
$R_{11}$ is H or alkyl;
$R_{12}$ is selected from OH, COOH, CO-alkyl, phenyl, morpholino, $NH_2$, NH-alkyl, N-(alkyl)$_2$ NH(NH) $NH_2$, $CH_2COO$-alkyl,
$R_{13}$ is selected from OH, and phenyl;
$R_{14}$ is selected from H, alkyl, cycloalkyl, aryl, and arylalkyl, wherein the cycloalkyl or aryl ring may comprise one or two heteroatoms in the cyclic structure selected from N and O and may be substituted with one or more substituent selected from alkyl, halo, cyano, amino, alkyl amino, dialkyamino, nitro, trifluoromethyl, aryl, alkyl-aryl, acyl, alkyloxy or aryloxy;
$R_{15}$ represents a group selected from H, halo, OH and alkoxy;
$R_{16}$ represents a group selected from alkyl, hydroxyalkyl, aryl, heteroaryl and arylalkyl;
one of $Q_1$ and $Q_2$ is CH and the other N;
$Q_3$ is selected from O, S, N and NH;
$Q_4$ is selected from C and N, and CO;
$Q_5$ is selected from C and N;
n is 0, 1 or 2;
p is 1, 2, 3 or 4;
q is 0, 1, 2, 3 or 4;
r is 0, 1, 2, 3 or 4;
s is 0, 1, 2 or 3;
or a pharmaceutically acceptable salt thereof In the above general formulae (1) or (2):
Alkyl denotes a straight-chain or branched group containing 1, 2, 3, 4, 5 or 6 carbon atoms. Examples of suitable alkyl radicals are methyl, ethyl, n-propyl, isopropyl, n-butyl, isobutyl, sec-butyl, tert-butyl, neopentyl etc.
Alkyl preferably comprises not more than 4 carbon atoms.
Cycloaklyl denotes a cyclic alkyl group comprising from 3 to 12 carbon atoms that may be mono- or bicyclic or bridged.
Preferred groups are cyclopropyl, cyclopentyl, cyclohexyl and adamantyl.
Aryl denotes an aromatic mono or bicyclic group comprising from 5 to 10 carbon atoms, namely phenyl, benzyl, toluyl, etc.
Aryl is preferably phenyl.
Alkyl amino and di-aklyl amino represent respectively groups of formula —NRR' wherein R is H and R' is alkyl (mono-amino) or both R and R' identical or different represent alkyl.
Arylalkyl represent a group of formula —RR' wherein R is an straight or branched chain containing 1, 2, 3, 4, 5 or 6 carbon atoms, preferably from 1 to 4 carbon atoms and R' is an aryl group as defined above.
Alkylaryl represents a group of formula —RR' wherein R is an aryl moiety and R' is a straight or branched alkyl group containing 1, 2, 3, 4, 5 or 6 carbon atoms as defined above, preferably from 1 to 4 carbon atoms.
Acyl represents a group of formula RCO—, wherein R is an alkyl or aryl group as defined above.
Alkyloxy represents a group of formula —OR, wherein R is an alkyl as defined above.
Aryloxy represents a group of formula —OR', wherein R' is an aryl as defined above.
Hydroxyalkyl represents a group of formula —ROH, wherein R is a straight or branched alkyl chain containing 1, 2, 3, 4, 5 or 6 carbon atoms as defined above.
Hydroxyaryl represents a group of formula —R'OH, wherein R' is an aryl moiety as defined above.
Halo denotes a halogen atom selected from the group consisting of fluoro, chloro, bromo and iodo in particular fluoro or chloro.
5-member heteroaromatic groups are preferably selected from a group consisting of pyrazole, isoxazole, triazole, oxazole, thiazole, imidazole, thiophenyl, and. furanyl;
6-member heteroaromatic groups are preferably selected from a group consisting of pyridyl, pyridazine and pyrimidinyl.
5 member heteroaromatic groups comprising 2 or 3 N atoms are preferably selected from pyrazolyl, imidazolyl, and triazolyl, and are most preferably 1H-imidazolyl and 1H-1,2,4-triazolyl.
Most preferred compounds according to the invention are compounds bearing one or several of the following features:
X is CO—NH or X represents a triazolyl ring, preferably a 1H-1,2,4-triazolyl ring,
Y is $SO_2$,
Q is a group of formula:

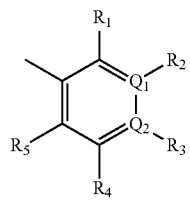

$R_1$ represents OH, $R_2$ is selected from H, halo and $OR_{11}$, $R_3$ is selected from H and halo $R_3$ is selected from H, $R_4$ is selected from H, alkyl, halo, CO-alkyl ($C_1$-$C_6$), CN, trifluoromethyl, CO-alkyl, phenyl and benzyl; $R_5$ is H; or
$R_1$ represents OH or halo and two from $R_2$ and $R_3$ or $R_3$ and $R_4$ or $R_4$ and $R_5$ together with the carbon atoms to which they are attached form an aromatic ring comprising 5 to 6 members, and the others from $R_2$ to $R_5$ represent H,
Q is a group of formula Q is selected from a group of formula:

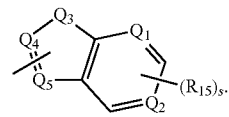

$R_{15}$ is a halogen atom, preferably chloro, fluoro or bromo,
$R_7$ and $R_8$ are alkyl, preferably methyl; $R_7$ is H and $R_8$ hydroxyalkyl, preferably hydroxyethyl, or $R_7$ is H or alkyl, e.g. methyl and $R_8$ is cycloalkyl, preferably cyclohexyl or adamantyl; or $R_7$ is H and $R_8$ is selected from pyrydyl, preferably 2-pyrydyl, phenylethyl and phenylbutyl; or $R_7$ and $R_8$ together with the N atom to which they are attached form a group of formula:

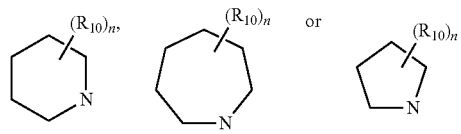

wherein $R_{10}$ and n are as defined above and $R_{10}$ is preferably alkyl, hydroxyl, halo, hydroxyalkyl, or
$R_7$ and $R_8$ together with the N atom to which they are attached form a group of formula:

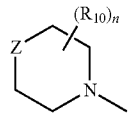

wherein Z is $NR_{14}$ and $NR_{14}$ is selected from phenyl, benzyl and pyrimidyl, preferably 2-pyrimidyl;
n is 0 or 1;
q is 1, 2 or 3;
r is 0, 1, 2, 3 or 4;
s is 0, 1 or 2;
Other preferred compounds of formula (1) are those wherein:
X is CO—NH or triazolyl, preferably a 1H-1,2,4-triazolyl ring
Y is $SO_2$,
$Q_1$ and $Q_2$ are CH
$R_1$ represents OH,
$R_2$ represents H,
$R_3$ and $R_4$ are as defined in claim 1 with the proviso that one from $R_3$ and $R_4$ is H;
$R_5$ is H; or
$R_1$ represents OH, and two from $R_2$ and $R_3$ or $R_3$ and $R_4$ or $R_4$ and $R_5$ together with the carbon atoms to which they are attached form an aromatic ring comprising 5 to 6 members, and the others from $R_2$ to $R_5$ represent H, or $R_7$ and $R_8$ represent alkyl, preferably methyl, or $R_7$ and $R_8$ together with the N atom to which they are attached form a group of formulae:

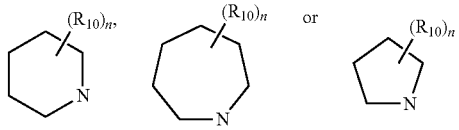

wherein $R_{10}$ is a defined in claim 1 and preferably alkyl, hydroxyl, halo or hydroxyalkyl, or $R_7$ and $R_8$ together with the N atom to which they are attached form a group of formula:

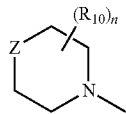

wherein Z is a $NR_{14}$ group, wherein $R_{14}$ is selected from phenyl, benzyl and pyrimidyl, preferably 2-pyrimidyl, or $R_7$ is H and $R_8$ is cycloalkyl, preferably cyclohexyl and adamantyl, n is 1, A particularly preferred group of compounds those of general formula (2a)

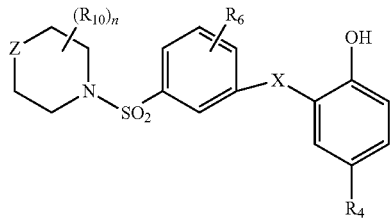

wherein X, Z, $R_4$, $R_6$ and $R_{10}$ and n are as defined above.

Another particularly preferred group of compounds those of general formula (2b)

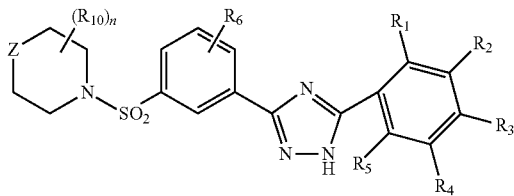

wherein, Z, $R_{1-5}$, $R_6$, and $R_{10}$ and n are as defined above.

Another particularly preferred group of compounds those of general formula 2c)

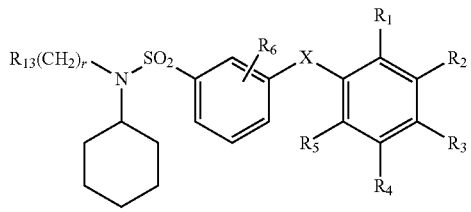

wherein, Z, $R_{1-5}$, $R_6$, $R_{13}$, and r are as defined above.

Another particularly preferred group of compounds those of general formula of general formula 2(d)

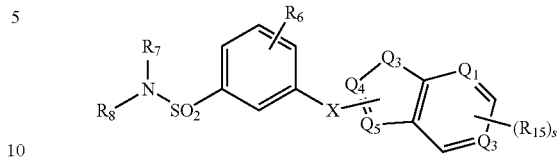

wherein $Q_1$, $Q_2$, $R_6$, $R_7$, $R_8$ are as defined above and X represents a bond, CONH or NH.

Most preferred compounds are the following:

N-(5-chloro-2-hydroxy-phenyl)-3-(1-piperidylsulfonyl)benzamide;

N-(5-fluoro-2-hydroxy-phenyl)-3-(1-piperidylsulfonyl)benzamide;

N-(5-bromo-2-hydroxy-phenyl)-3-(1-piperidylsulfonyl)benzamide;

N-(2-hydroxy-5-phenyl-phenyl)-3-(1-piperidylsulfonyl)benzamide;

N-(5-benzyl-2-hydroxy-phenyl)-3-(1-piperidylsulfonyl)benzamide;

N-[2-hydroxy-5-(trifluoromethyl)phenyl]-3-(1-piperidylsulfonyl)benzamide;

N-(5-cyano-2-hydroxy-phenyl)-3-(1-piperidylsulfonyl)benzamide;

N-(5-acetyl-2-hydroxy-phenyl)-3-(1-piperidylsulfonyl)benzamide;

N-[5-(1,1-dimethylpropyl)-2-hydroxy-phenyl]-3-(1-piperidylsulfonyl)benzamide;

N-(2-hydroxy-4-methoxy-phenyl)-3-(1-piperidylsulfonyl)benzamide;

N-(3-hydroxy-2-naphthyl)-3-(1-piperidylsulfonyl)benzamide;

N-(2-hydroxy-1-naphthyl)-3-(1-piperidylsulfonyl)benzamide;

N-(5-chloro-2-hydroxy-phenyl)-3-(piperidine-1-carbonyl)benzamide;

5-chloro-2-hydroxy-N-[3-(1-piperidylsulfonyl)phenyl]benzamide;

N-(5-chloro-2-hydroxy-phenyl)-4-methyl-3-(1-piperidylsulfonyl)benzamide;

N-(5-chloro-2-hydroxy-phenyl)-3-(dimethylsulfamoyl)benzamide;

N-(5-chloro-2-hydroxy-phenyl)-3-(cyclohexylsulfamoyl)benzamide;

3-(azepan-1-ylsulfonyl)-N-(5-chloro-2-hydroxy-phenyl)benzamide;

N-(5-chloro-2-hydroxy-phenyl)-3-[(2-methyl-1-piperidyl)sulfonyl]benzamide;

N-(5-chloro-2-hydroxy-phenyl)-3-[(3-methyl-1-piperidyl)sulfonyl]benzamide;

N-(5-chloro-2-hydroxy-phenyl)-3-[(4-methyl-1-piperidyl)sulfonyl]benzamide;

3-[(4-benzyl-1-piperidyl)sulfonyl]-N-(5-chloro-2-hydroxyphenyl)benzamide;

N-(5-chloro-2-hydroxy-phenyl)-3-[[4-(1-piperidyl)-1-piperidyl]sulfonyl]benzamide;

N-(5-chloro-2-hydroxy-phenyl)-3-(4-methylpiperazin-1-yl)sulfonyl-benzamide;

N-(5-chloro-2-hydroxy-phenyl)-3-(4-phenylpiperazin-1-yl)sulfonyl-benzamide;

3-(4-benzylpiperazin-1-yl)sulfonyl-N-(5-chloro-2-hydroxyphenyl)benzamide;

N-(5-chloro-2-hydroxy-phenyl)-4-(1-piperidylsulfonyl)benzamide;
N-(5-chloro-1H-indol-7-yl)-3-(1-piperidylsulfonyl)benzamide;
5-chloro-3-[3-(1-piperidylsulfonyl)benzoyl]-1H-benzimidazol-2-one;
3-(1-adamantylsulfamoyl)-N-(5-chloro-2-hydroxy-phenyl)benzamide;
N-(5-chloro-2-hydroxy-phenyl)-3-[cyclohexyl(methyl)sulfamoyl]benzamide;
N-(5-chloro-2-hydroxy-phenyl)-3-[[2-(hydroxymethyl)-1-piperidyl]sulfonyl]benzamide;
N-(5-chloro-2-hydroxy-phenyl)-3-(4-pyrimidin-2-ylpiperazin-1-yl)sulfonyl-benzamide;
N-(5-chloro-2-hydroxy-phenyl)-3-[(3-phenyl-1-piperidyl)sulfonyl]benzamide;
N-(5-chloro-2-hydroxy-phenyl)-3-[[3-(hydroxymethyl)-1-piperidyl]sulfonyl]benzamide;
N-(5-chloro-2-hydroxy-phenyl)-3-pyrrolidin-1-ylsulfonyl-benzamide;
N-(5-chloro-2-hydroxy-phenyl)-3-morpholinosulfonyl-benzamide;
N-(5-chloro-2-hydroxy-phenyl)-3-indolin-1-ylsulfonyl-benzamide;
N-(2-chlorophenyl)-3-(1-piperidylsulfonyl)benzamide;
N-(2,5-dichlorophenyl)-3-(1-piperidylsulfonyl)benzamide;
N-(5-chloro-2-hydroxy-phenyl)-N-methyl-3-(1-piperidylsulfonyl)benzamide;
N-(5-chloro-2-fluoro-phenyl)-3-(1-piperidylsulfonyl)benzamide;
N-(4-chloro-2-hydroxy-phenyl)-3-(1-piperidylsulfonyl)benzamide;
2-chloro-N-(5-chloro-2-hydroxy-phenyl)-5-(1-piperidylsulfonyl)benzamide;
N-[(1S,2S)-2-hydroxycyclohexyl]-3-(1-piperidylsulfonyl)benzamide;
N-(5-chloro-2-hydroxy-phenyl)-2-fluoro-5-(1-piperidylsulfonyl)benzamide;
N-(5-chloro-2-hydroxy-phenyl)-3-(cyclohexylsulfamoyl)-4-methyl-benzamide;
N-(5-chloro-2-hydroxy-phenyl)-3-(2-pyridylsulfamoyl)benzamide;
N-(5-chloro-2-hydroxy-phenyl)-2-methyl-5-(1-piperidylsulfonyl)benzamide;
N-[(2-hydroxyphenyl)methyl]-3-(1-piperidylsulfonyl)benzamide;
N-(4-hydroxy-3-pyridyl)-3-(1-piperidylsulfonyl)benzamide;
2-hydroxy-N-(2-hydroxyphenyl)-5-(1-piperidylsulfonyl)benzamide;
N-(5-chloro-2-hydroxy-phenyl)-3-(2-phenylethylsulfamoyl)benzamide;
N-(5-chloro-2-hydroxy-phenyl)-3-(4-phenylbutylsulfamoyl)benzamide;
N-(5-chloro-2-hydroxy-phenyl)-3-(2-hydroxyethylsulfamoyl)benzamide;
N-(3-chlorophenyl)-2-hydroxy-5-(1-piperidylsulfonyl)benzamide;
4-chloro-2-[[3-(1-piperidylsulfonyl)phenyl]methylamino]phenol;
N-[3-(1-piperidylsulfonyl)phenyl]-1H-indazol-3-amine;
4-chloro-2-[2-[3-(1-piperidylsulfonyl)phenyl]-1H-imidazol-5-yl]phenol;
3-[benzyl(cyclohexyl)sulfamoyl]-N-(5-chloro-2-hydroxy-phenyl)benzamide;
tert-butyl 2-[[3-[(5-chloro-2-hydroxy-phenyl)carbamoyl]phenyl]sulfonyl-cyclohexyl-amino]acetate;
N-(5-chloro-2-hydroxy-phenyl)-3-[cyclohexyl(3-phenylpropyl)sulfamoyl]benzamide;
N-(5-chloro-2-hydroxy-phenyl)-3-(4-hydroxybutylsulfamoyl)benzamide;
2-[[3-[(5-chloro-2-hydroxy-phenyl)carbamoyl]phenyl]sulfonyl-cyclohexyl-amino]acetic acid
2-[3-(1-piperidylsulfonyl)phenyl]-3H-benzimidazol-4-ol;
N-(5-chloro-2-hydroxy-phenyl)-2-(1-piperidylsulfonyl)benzamide;
N-(5-chloro-2-hydroxy-phenyl)-3-(cyclohexylsulfonylamino)benzamide;
3-[3-aminopropyl(cyclohexyl)sulfamoyl]-N-(5-chloro-2-hydroxy-phenyl)benzamide;
N-(3-aminopropyl)-3-(5-chloro-1,3-benzoxazol-2-yl)-N-cyclohexyl-benzenesulfonamide;
N-(5-chloro-2-hydroxy-phenyl)-3-[cyclohexyl(3-guanidinopropyl)sulfamoyl]benzamide;
N-(5-chloro-2-hydroxy-phenyl)-2-(1-piperidylsulfonylmethyl)benzamide;
N-(4,5-dichloro-2-hydroxy-phenyl)-3-(1-piperidylsulfonyl)benzamide;
5-chloro-N-[3-(1-piperidylsulfonyl)phenyl]-1H-indazol-3-amine;
N-(3-chloro-2-hydroxy-phenyl)-3-(1-piperidylsulfonyl)benzamide;
3-chloro-8-(1-piperidylsulfonyl)-5H-benzo[b][1,4]benzoxazepin-6-one;
N-[(5-chloro-2-hydroxy-phenyl)methyl]-3-(1-piperidylsulfonyl)benzamide;
3-chloro-8-(1-piperidylsulfonyl)-5,11-dihydrobenzo[b][1,4]benzodiazepin-6-one;
5-chloro-2-[3-(1-piperidylsulfonyl)phenyl]-1,3-benzoxazole;
4-chloro-2-[3-[3-(1-piperidylsulfonyl)phenyl]-1H-1,2,4-triazol-5-yl]phenol;
7-chloro-2-[3-(1-piperidylsulfonyl)phenyl]-3H-benzimidazo-4-ol;
5,7-dichloro-2-[3-(1-piperidylsulfonyl)phenyl]-3H-benzimidazol-4-ol;
N-(5-chloro-2-hydroxy-phenyl)-3-(1-piperidylsulfonylmethyl)benzamide;
N-(5-chloro-2-hydroxy-phenyl)-2-(cyclohexylsulfonylamino)benzamide;
4-[[3-[(5-chloro-2-hydroxy-phenyl)carbamoyl]phenyl]sulfonyl-cyclohexyl-amino]butanoic acid;
N-(5-chloro-2-hydroxy-phenyl)-3-[cyclohexyl(5-phenylpentyl)sulfamoyl]benzamide;
N-(5-chloro-2-hydroxy-phenyl)-3-[cyclohexyl(3-hydroxypropyl)sulfamoyl]benzamide;
N-(5-chloro-2-hydroxy-phenyl)-2-[2-(1-piperidylsulfonyl)phenyl]acetamide;
N-(5-chloro-2-hydroxy-phenyl)-3-methyl-5-(1-piperidylsulfonyl)benzamide;
N-(5-chloro-2-hydroxy-phenyl)-6-(cyclohexylsulfonylamino)pyridine-2-carboxamide;
N-(5-chloro-2-hydroxy-phenyl)-5-(cyclohexylsulfonylamino)pyridine-3-carboxamide;
N-(5-chloro-2-hydroxy-phenyl)-3-[cyclopentyl(methyl)sulfamoyl]benzamide;
N-(5-chloro-2-hydroxy-phenyl)-1,1-dioxo-2,3-dihydro-1,2-benzothiazole-6-carboxamide;
3-[2-aminoethyl(cyclohexyl)sulfamoyl]-N-(5-chloro-2-hydroxy-phenyl)benzamide;
N-(2-aminoethyl)-3-(5-chloro-1,3-benzoxazol-2-yl)-N-cyclohexyl-benzenesulfonamide;
3-[4-aminobutyl(cyclohexyl)sulfamoyl]-N-(5-chloro-2-hydroxy-phenyl)benzamide;

N-(4-aminobutyl)-3-(5-chloro-1,3-benzoxazol-2-yl)-N-cyclohexyl-benzenesulfonamide;
N-(5-chloro-2-hydroxy-phenyl)-3-[cycloheptyl(methyl)sulfamoyl]benzamide;
N-(3-aminopropyl)-3-[5-(5-chloro-2-hydroxy-phenyl)-1H-1,2,4-triazol-3-yl]-N-cyclohexyl-benzenesulfonamide;
N-(5-chloro-2-hydroxy-phenyl)-3-(cyclohexylsulfonylamino)-5-methoxy-benzamide;
N-(5-chloro-2-hydroxy-phenyl)-3-[cyclohexyl-[3-(dimethylamino)propyl]sulfamoyl]benzamide;
3-(5-chloro-1,3-benzoxazol-2-yl)-N-cyclohexyl-N-[3-(dimethylamino)propyl]benzenesulfonamide;
3-[3-aminopropyl(cyclohexyl)sulfamoyl]-N-methyl-benzamide;
4-chloro-2-[4-[3-(1-piperidylsulfonyl)phenyl]triazol-1-yl]phenol;
3-[3-aminopropyl(cyclohexyl)sulfamoyl]-N-(3-chlorophenyl)benzamide;
N-(3-aminopropyl)-3-bromo-N-cyclohexyl-benzenesulfonamide;
3-[3-aminopropyl(cyclohexyl)sulfamoyl]benzamide;
4-chloro-2-[4-[3-(1-piperidylsulfonyl)phenyl]pyrimidin-2-yl]phenol;
3-[3-aminopropyl(cyclohexyl)sulfamoyl]-N-phenyl-benzamide;
N-(3-aminopropyl)-3-(1,3-benzothiazol-2-yl)-N-cyclohexyl-benzenesulfonamide;
3-[3-aminopropyl(cyclohexyl)sulfamoyl]-N-(2-methoxyphenyl)benzamide;
N-(3-aminopropyl)-N-cyclohexyl-3-(1H-tetrazol-5-yl)benzenesulfonamide;
3-(1,3-benzoxazol-2-yl)-N-cyclohexyl-N-methyl-benzenesulfonamide;
3-[3-aminopropyl(cyclohexyl)sulfamoyl]-N-(2-hydroxyphenyl)benzamide;
N-(3-aminopropyl)-3-(1,3-benzoxazol-2-yl)-N-cyclohexyl-benzenesulfonamide;
3-[3-aminopropyl(cyclohexyl)sulfamoyl]-N,N-dimethyl-benzamide;
3-[3-aminopropyl(cyclohexyl)sulfamoyl]-N-(2-hydroxy-3-methoxy-phenyl)benzamide;
N-(3-aminopropyl)-N-cyclohexyl-3-(7-methoxy-1,3-benzoxazol-2-yl)benzenesulfonamide;
N-(3-aminopropyl)-N-cyclohexyl-3-thiazolo[5,4-b]pyridin-2-yl-benzenesulfonamide;
2-[3-(1-piperidylsulfonyl)phenyl]benzotriazole;
N-(3-aminopropyl)-N-cyclohexyl-3-thiazolo[4,5-c]pyridin-2-yl-benzenesulfonamide;
N-(3-aminopropyl)-N-cyclohexyl-3-(7-hydroxy-1,3-benzoxazol-2-yl)benzenesulfonamide;
3-[3-aminopropyl(cyclohexyl)sulfamoyl]-N-(4,5-dichloro-2-hydroxy-phenyl)benzamide;
N-(3-aminopropyl)-N-cyclohexyl-3-(5,6-dichloro-1,3-benzoxazol-2-yl)benzenesulfonamide;
N-(3-aminopropyl)-3-(1H-benzimidazol-2-yl)-N-cyclohexyl-benzenesulfonamide;
N-(3-aminopropyl)-3-bromo-N-methyl-benzenesulfonamide;
N-(3-aminopropyl)-3-bromo-N-cyclohexyl-benzamide;
N-(3-aminopropyl)-2-bromo-N-cyclohexyl-benzenesulfonamide;
N-(3-aminopropyl)-4-bromo-N-cyclohexyl-benzenesulfonamide;
N'-[(3-bromophenyl)methyl]-N'-cyclohexyl-propane-1,3-diamine;
N-(5-chloro-2-hydroxy-phenyl)-3-[cyclohexyl(3-morpholinopropyl)sulfamoyl]benzamide;
3-(5-chloro-1,3-benzoxazol-2-yl)-N-cyclohexyl-N-(3-morpholinopropyl)benzenesulfonamide;
3-(5-chloro-1,3-benzoxazol-2-yl)-N-cyclohexyl-N-(3-hydroxypropyl)benzenesulfonamide;
N-(3-aminopropyl)-N-cyclohexyl-benzenesulfonamide;
3-[5-(5-chloro-2-hydroxy-phenyl)-1H-1,2,4-triazol-3-yl]-N-cyclohexyl-N-methyl-benzenesulfonamide;
N-[5-chloro-2-hydroxy-4-(2-methoxyethoxy)phenyl]-3-(1-piperidylsulfonyl)benzamide;
N-(5-chloro-2-hydroxy-phenyl)-3-[cycloheptyl(methyl)sulfamoyl]benzamide;
(2-amino-4-chloro-phenyl)methyl 3-(1-piperidylsulfonyl)benzoate;
N-(2-acetamido-5-chloro-phenyl)-3-(1-piperidylsulfonyl)benzamide;
ethyl 4-chloro-2-[[3-(1-piperidylsulfonyl)benzoyl]amino]benzoate;
N-(5-chloro-2-hydroxy-phenyl)-3-[(4-hydroxy-1-piperidyl)sulfonyl]benzamide;
4-chloro-2-[[3-(1-piperidylsulfonyl)benzoyl]amino]benzoic acid;
N-(3,5-dichloro-2-hydroxy-phenyl)-3-(1-piperidylsulfonyl)benzamide;
N-[5-chloro-2-(hydroxymethyl)phenyl]-3-(1-piperidylsulfonyl)benzamide;
N-(5-chloro-1H-benzimidazol-2-yl)-3-(1-piperidylsulfonyl)benzamide;
N-(5-chloro-2-hydroxy-phenyl)-3-[(4,4-difluoro-1-piperidyl)sulfonyl]benzamide;
N-(3-acetyl-5-chloro-2-hydroxy-phenyl)-3-(1-piperidylsulfonyl)benzamide;
N-(5-chloro-2-hydroxy-3-methyl-phenyl)-3-(1-piperidylsulfonyl)benzamide;
N-[5-chloro-2-(1H-tetrazol-5-yl)phenyl]-3-(1-piperidylsulfonyl)benzamide;
N-[5-chloro-2-(N-hydroxycarbamimidoyl)phenyl]-3-(1-piperidylsulfonyl)benzamide;
N-(5-chloro-3-fluoro-2-hydroxy-phenyl)-3-(1-piperidylsulfonyl)benzamide;
[4-chloro-2-[[3-(1-piperidylsulfonyl)benzoyl]amino]phenyl] dihydrogen phosphate;

The invention further pertains to compounds of general formula (1)

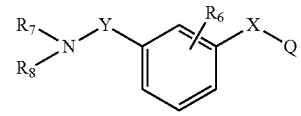

wherein all the substituents are as defined previously, for use as medicines, namely for the treatment of pain disorders, cancer or autoimmune disorders.

Compounds of formula (1) can be prepared using conventional procedures such as by the following illustrative methods in which the various substituents are as previously defined for the compounds of the formula (1) unless otherwise stated.

According to a first method, compounds of formula (1) wherein X represents CONH, Y represents SO$_2$ and R$_7$ and R$_8$ together with the N atom to which they are attached form a group of formula:

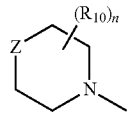

are prepared by a method comprising the following steps:

(i) Reacting a compound of formula (3)

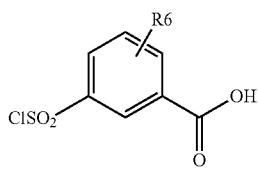

with a compound of general formula (4)

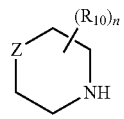

to obtain a compound of formula (5)

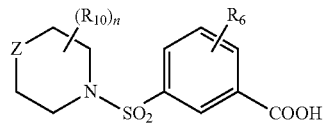

(ii) Reacting the compound of formula (5) with a compound of formula (6)

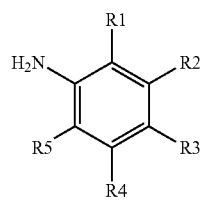

to obtain a compound of formula (7)

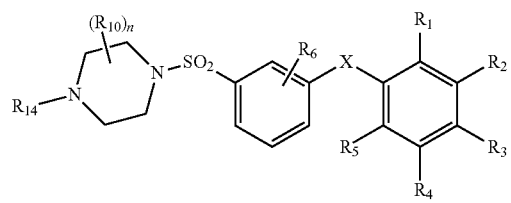

According to a second method, compounds of formula (1) wherein Q is a group of formula

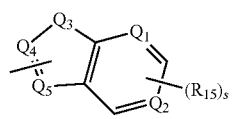

And Y represents SO$_2$ and R$_7$ and R$_8$ together with the N atom to which they are attached form a group of formula:

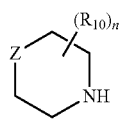

are prepared by reacting a compound of formula (8)

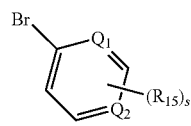

with a compound of general formula (9) in a Buchwald-Hartwig cross coupling reaction

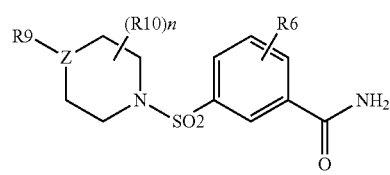

Compounds of general formula (9) may be obtained by reacting compounds of formula (10)

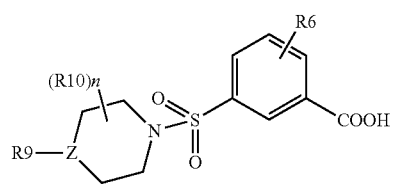

with N, N-carbonyl diimidazole in presence of ammonium acetate.

According to a third method, compounds of formula (1) wherein R$_1$ together with X forms a heterocyclic aromatic or non aromatic ring and Y represents SO$_2$ are prepared according to the following steps:

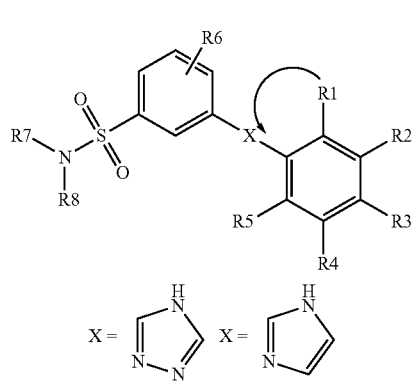

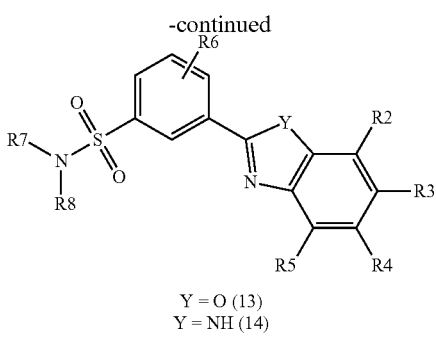

Y = O (13)
Y = NH (14)

The compounds provided here herein may be prepared from known or commercially available starting materials and reagents by one skilled in the art of organic synthesis. Such procedures include recrystallization, column chromatography or HPLC. The following schemes are presented with details as to the preparation of representative substituted triazol (11), imidazol (12), benzoxazol (13) or benzimidazol (14)

Other compounds within the scope of the invention are prepared according to the following reaction schemes.

General Synthetic Scheme for the Preparation of 5-Aryl-triazol-3-yl-N-benzenesulfonamide Derivatives According to the above reaction scheme, a benzohydrazide derivative 16 is reacted with a benzamidine derivatives 18 to produce the triazole compounds of the general formula 11. This reaction is preferably carried out overnight in a mixture of EtOH and chlorobenzene 1/1 at 105° C.

The benzamidine derivative 18 could be obtained easily from the corresponding benzonitrile derivative 17 in the presence of LiHMDS according to publication in organic process & development, 2009, 13, 1206-1208.

The benzohydrazide derivative 16 can be prepared from readily available 3-chlorosulfonyle benzoic ester derivatives 15 in a two steps sequence.

Additionally, conventional protecting groups may be necessary to prevent certain functional groups from undergoing undesired reactions. The choice of a suitable protecting group for a particular functional group as well as suitable conditions for protection and deprotection are well known in the art. For example, numerous protecting group, and their introduction and removal, are described in T. W. Greene and P. G. M. Wutz, Protecting groups in Organic synthesis, Third Edition, Wiley, Ney York, 1999, and references cited therein.

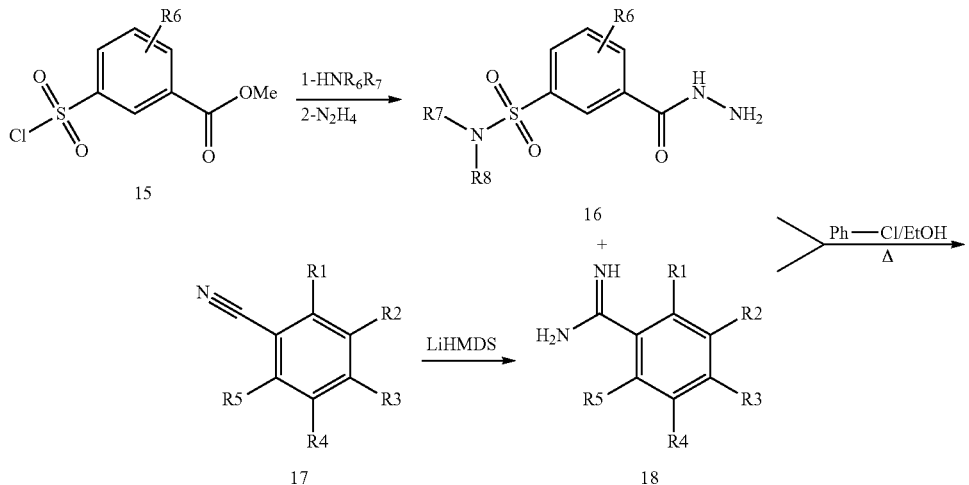

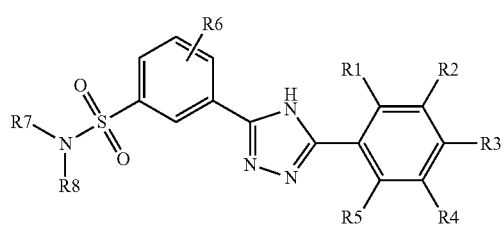

General Synthetic Scheme for the Preparation of
4-Aryl-3-imidazol-2yl-N-benzenesulfonamide
Derivatives

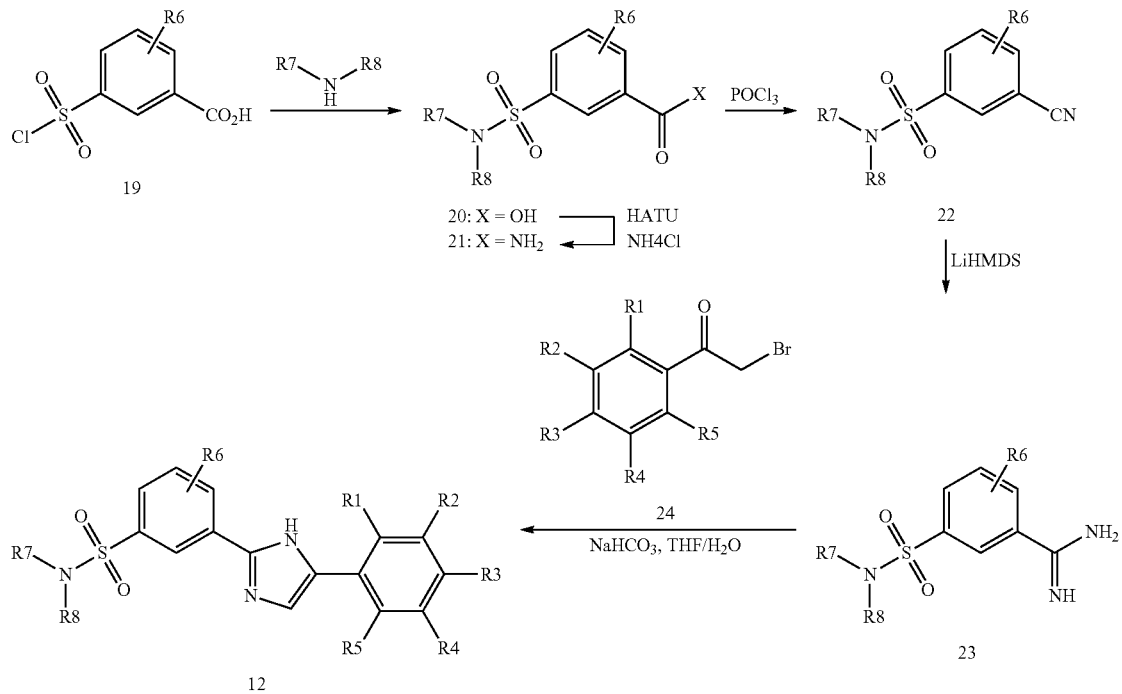

According to the above reaction scheme, a benzamidine derivative of the general formula 23 is reacted with a suitably substituted phenacyl bromide derivatives 24 to produce the imidazole compounds of the general formula 12 in the presence of a base, for example sodium hydrogenocarbonate. Following the procedure according to scheme 2, compounds of the general formula 23 can be prepared in a four step sequence from 3-chlorosulfonyle benzoic acid derivative 19 following classical literature procedures.

General Synthetic Scheme for the Preparation of
3-(benzoxazol-2yl) N-arylsulfonamide Derivatives

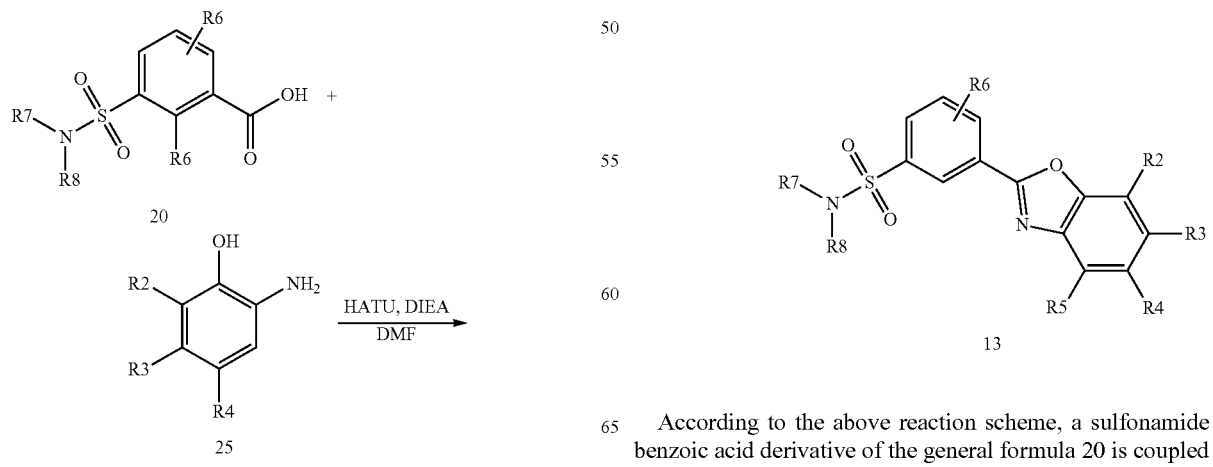

According to the above reaction scheme, a sulfonamide benzoic acid derivative of the general formula 20 is coupled with a suitably substituted 2-Hydroxy-aniline derivative 25 to produce the corresponding-N-(2-hydroxyphenyl) benzamide derivative of the general formula 26. For example, coupling reagent like HATU in presence of the Hünig base (N-ethyldiisopropylamine) can be employed in presence of an inert solvent (DMF) for the formation of such amide bond. 3-(benzoxazol-2yl) N-arylsulfonamide derivatives of the general formula 13 can be obtained by cyclisation of 22 using the vast array of possibilities known in the art. A convenient method is the use of TFA under microwave irradiations.

General Synthesis for the Preparation of N-(3-sulfamoylphenyl)benzamide Derivatives 32

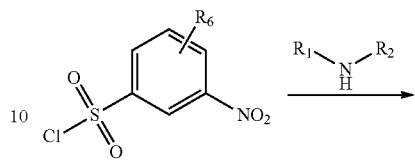

29

General Synthetic Scheme for the Preparation of 3-(benzimidazol-2yl) N-arylsulfonamide Derivatives

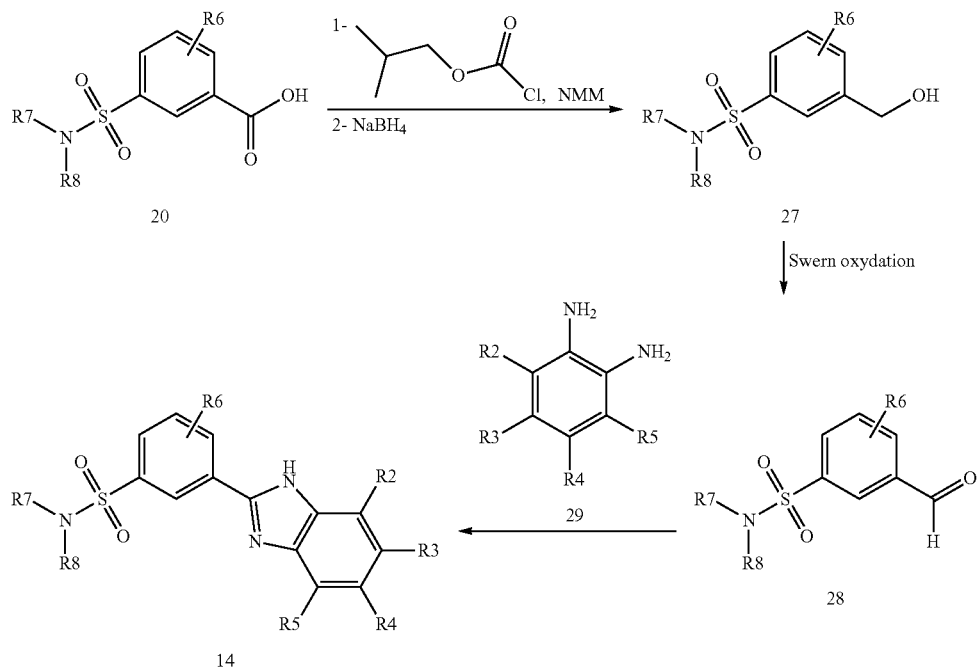

According to the above reaction scheme, a 3-formyl arylsulfonamide derivative of the general formula 28 is reacted with a suitably benzene 1-2 diamine derivatives 29 to produce benzimidazole derivative of the general formula 14. A convenient method involves the use of disodium metabisulfite $Na_2S_2O_5$ in a protic solvent ($EtOH/H_2O$). This protocol leads to a better yield of benzimidazoles under milder condition.

3-formyl benzenesulfonamide derivative 28 can be prepared in a two-step sequence from 3-chlorosulfonyle benzoic acid derivatives 20 following literature procedures. For example, the carboxylic acid derivative 20 was converted to the mixed anhydride with isobutyl chloroformate and reduced in situ with sodium borohydride, to provide the corresponding primary alcohol derivative 27. Oxydation of the primary alcohol derivative 27 under Swern conditions (Oxalyl chloride, $NEt_3$, DMSO, −78° C.) led to the aldehyde derivative 28.

-continued

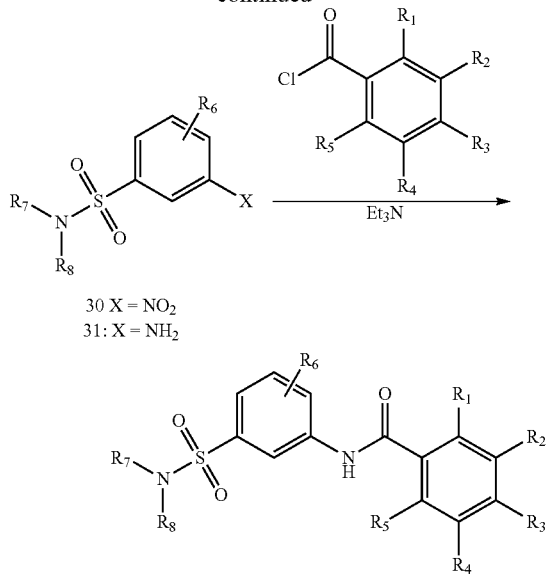

30 X = NO$_2$
31: X = NH$_2$

32

According to the above reaction scheme, a 3-sulfonylaniline derivative of the general formula 31 is coupled with a suitably substituted acylchloride to produce the corresponding-N-(3-sulfamoylphenyl)benzamide derivatives of the general formula 32.

General Synthesis for the Preparation of
3-(N-cycloalkyl-N-alkylsulfamoyl)benzamide
Derivatives 33

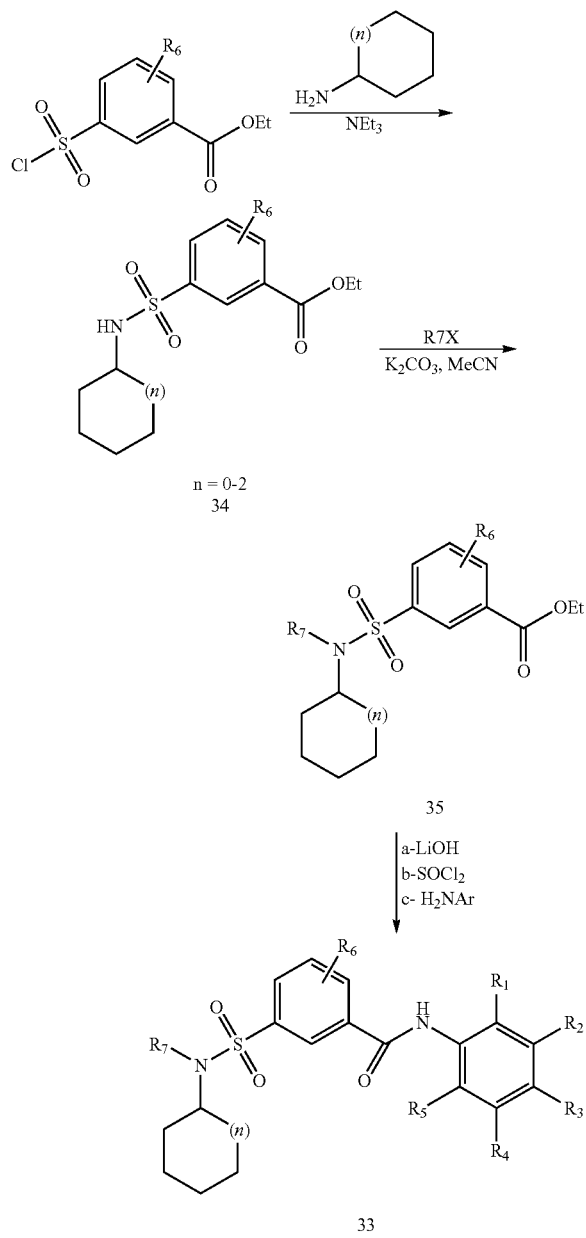

According to the above reaction scheme, a 3-cycloalkylsulfamoylbenzoate derivative of the general formula 34 is alkylated with a suitably substituted halogenoalkyl derivative to produce the corresponding —N-(3-sulfamoyl-N-alkyl)benzamide derivatives of the general formula 35. Derivatives 33 can be prepared in a three-step sequence from derivatives 35 following literature procedures.

The pharmacological activity of the compounds may be assessed by the following tests:
Covalent Labeling of Cells Expressing the SNAP Tagged-FLT3
Labelling of Adherent Cells
Cell culture medium was removed from the 96 well plates and 100 nM of SNAP-Lumi4 Tb previously diluted in the Tag-lite labelling medium, was added under 100 µl per well, and further incubated 1 h at 37° C. under 5% CO2. The excess of SNAP-Lumi4-Tb was removed by washing each well 4 times with 100 µl of Tag-lite labelling medium.
Labelling of a Batch of Cells and Cells Freezing
After removal of the cell culture medium from a flask containing adherent cells, 5 ml of Tag-lite labelling medium containing 100 nM of SNAP-Lumi4-Tb was added to the flask and incubated for 1 h at 37° C. under 5% $CO_2$. The excess of SNAP-Lumi4-Tb was removed by washing each flask 4 times with 5 ml of Tag-lite labelling medium. Cells were detached, pelleted by centrifugation (5 min at 1,300 rpm) and suspended in a cell culture medium containing 10% DMSO. Then, cells were distributed at 5 millions cells per vial and slowly frozen to −80° C. in isopropanol then transferred in liquid nitrogen for storage.
Prior to their use, the frozen cells were thawed quickly at 37° C., the medium was removed from the vials and the cells were suspended in the Tag-lite labelling medium at a cell-density of 1 million cells/ml.
Tag-Lite Binding Assays
Tag-lite binding assays were performed 24 h after transfection on fresh cells. When using frozen cells, binding assays were carried out immediately after cells thawing. When the assay was carried out on adherent cells in 96-well plates, the cell density was 50,000 cells per well, while a density of 10,000 cells per well was used to carry out binding assays in suspension in 384-well small volume plates.
Saturation Binding Assay
Saturation binding experiments were performed by incubating the cells with increasing concentrations of Red-FL diluted in the Tag-lite labelling medium. For each concentration, non-specific binding was determined by adding 0.3 µM of unlabeled FL diluted in the same buffer. In plates containing labelled cells, 50 µl (or 10 µl in 384 wells plates) of Tag-lite labelling medium, 25 µl (or 5 µl for 384 well plates) of unlabeled FL or Tag-lite labelling medium were added, followed by the addition of 25 µl (or 5 µl in 384-well plates) Red-FL. Plates were incubated for 4 h or overnight at room temperature before signal detection.
Competition Binding Assay
Both Red-FL and the compounds to be tested were diluted in Tag-lite labelling medium. Cells were incubated with 0.5 nM Red-FL in the presence of increasing concentrations of compounds to be tested. In the plates containing labelled cells, 50 µl (or 10 µl in 384-well plates) of Tag-lite labelling medium, 25 µl (or 5 µl in 384-well plates) of compounds to be tested were added and incubated for 1 h at Room temperature prior to the addition of 25 µl (or 5 µl in 384-well plates) of Red-FL. Plates were then incubated at room temperature for 4 h or overnight before signal detection.
Auto-Phosphorylation Assays
Auto-phosphorylation assays were performed on RS4-11 cells that express endogenous FLT3 receptor. A density of 50,000 cells per well was used to carry out this assay in suspension in 384-well small volume plates to determine the degree of phosphorylation of FLT3. In the aim to discover antagonist compounds and to develop this assay, we were determined the efficiency of FL on RS4-11 cells.

Efficiency of FL

Rh-FL was diluted in Tag-lite labelling medium. Cells were incubated in the presence of increasing concentrations of rh-FL. In the plates containing RS4-11 cells (10 µl/well), 2 µl of rh-FL were added and incubated for 3 minutes at Room temperature. 4 µl per well of lysis buffer were added and incubated for 2 h at room temperature. A mix of anti-FLT3 and an anti-TYR-969 FLT3 antibodies labeled with Lumi4-Tb and d2 respectively (4 µl) diluted in Tag-lite labelling medium were added on cell lysate. Plates were then incubated at room temperature for 2 h or overnight before signal detection.

Competition Assay

Both rh-FL and the compounds to be tested were diluted in Tag-lite labelling medium. Cells were incubated with 0.1 µM of rh-FL in the presence of increasing concentrations of compounds to be tested. In the plates containing RS4-11 cells (5 µl/well), 5 µl of compounds to be tested were added and incubated for 1 h at Room temperature prior to the addition of 2 µl of rh-FL at 0.1 µM. After incubation of 3 minutes at room temperature of rh-FL, 4 µl of lysis buffer were added and incubated for 2 h at room temperature. A mix of anti-FLT3 and an anti-TYR-969 FLT3 antibodies labeled with Lumi4-Tb and d2 respectively (4 µl) diluted in Tag-lite labelling medium, were added on cell lysate. Plates were then incubated at room temperature for 2 h or overnight before signal detection.

Signal Detection

Signal was detected using an advanced fluorescence microplate reader (RUBYstar, BMG Labtech) equipped with a HTRF optic module allowing a donor excitation at 337 nm and a signal collection both at 665 nm and 620 nm. A frequency of 20 flashes/well is selected for the laser excitation. The signal was collected both at 665 nm and 620 nm using the following time-resolved settings: delay 50 µs, integration time 400 µs. HTRF ratios were obtained by dividing the acceptor signal (665 nm) by the donor signal (620 nm) and multiplying this value by 10,000. The 10,000 multiplying factor is used solely for the purpose of easier data handling.

Data Analysis and Statistics $K_d$ values of the fluorescent ligand were determined from saturation curves of the specific binding using GraphPad Prism software (GraphPad Software, Inc., San Diego, Calif.). $K_i$ values of the compounds were determined from binding competition experiments according to the Cheng and Prusoff equation. EC50 and IC50 values of the rh-FL and compounds were determined from sigmoidal dose-response curves using GraphPad Prism software (GraphPad Software, Inc., San Diego, Calif.).

Selectivity of a FLT3 receptor antagonists may be assayed for instance by carrying out biochemical kinase binding assays such as KinomeScan kinase binding assays as described in Fabian et al. 2005 and Karaman et al. 2008. For the FLT3 assay, a kinase construct that spanned the catalytic domain only (amino acids 592 to 969 in NP_004110.2) may be used. This construct does not include the juxtamembrane domain and is designed to measure the intrinsic binding affinity of the open FLT3 active site for inhibitors as previously described in Zarrinkar et al. 2009.

Pharmaceutically acceptable salts of the compounds of formula (1) include the acid addition and base salts thereof. Suitable acid addition salts are formed from acids, which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate and xinafoate salts.

For a review on suitable salts, see "Handbook of Pharmaceutical Salts: Properties, Selection, and Use" by Stahl and Wermuth (Wiley-VCH, Weinheim, Germany, 2002). Pharmaceutically acceptable salts of compounds of formula (1) may be prepared by one or more of three methods:
  (i) by reacting the compound of formula (1) with the desired acid or base;
  (ii) by removing an acid- or base-labile protecting group from a suitable precursor of the compound of formula (1) or by ring-opening a suitable cyclic precursor, for example, a lactone or lactam, using the desired acid or base; or
  (iii) by converting one salt of the compound of formula (1) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water. Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components, which may be in stoichiometric or non-stoichiometric amounts. The resulting complexes may be ionised, partially ionized, or non-ionized. For a review of such complexes, see J Pharm Sci, 64 (8), 1269-1288 by Haleblian (August 1975).

Hereinafter all references to compounds of formula (1) include references to salts, solvates and complexes thereof and to solvates and complexes of salts thereof.

The compounds of the invention include compounds of formula (1) as hereinbefore defined, including all polymorphs and crystal habits thereof, prodrugs and isomers thereof whenever relevant So-called 'pro-drugs' of the compounds of formula (1) are also within the scope of the invention. Thus certain derivatives of compounds of formula (1) which may have little or no pharmacological activity themselves can, when administered into or onto the body, be converted into compounds of formula (1) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T. Higuchi and W. Stella) and 'Bioreversible Carriers in Drug Design', Pergamon Press, 1987 (ed. E. B Roche, American Pharmaceutical Association).

Prodrugs in accordance with the invention can, for example, be produced by replacing appropriate functionalities present in the compounds of formula (1) with certain moieties known to those skilled in the art as 'pro-moieties' as described, for example, in "Design of Prodrugs" by H. Bundgaard (Elsevier, 1985).

Some examples of prodrugs in accordance with the invention include amides thereof, for example, a compound wherein, as the case may be the hydrogen of the amino functionality of the compound of formula (1) is/are replaced by $(C_1-C_{10})$alkanoyl.

Further examples of replacement groups in accordance with the foregoing examples and examples of other prodrug types may be found in the aforementioned references. Moreover, certain compounds of formula (1) may themselves act as prodrugs of other compounds of formula (1).

Also included within the scope of the invention are metabolites of compounds of formula (1), that is, compounds formed in vivo upon administration of the drug, such as a primary amino derivatives thereof or phenol derivative thereof, or carboxylic acid derivative Pharmaceutically acceptable solvates in accordance with the invention include those wherein the solvent of crystallization may be isotopically substituted, e.g. $D_2O$.

The compounds of formula (1), their pharmaceutically acceptable salts and/or derived forms, are valuable pharmaceutically active compounds, which are suitable for the therapy and prophylaxis of pain disorders.

The compounds of formula (1), their pharmaceutically acceptable salts and/or derived forms, are further valuable pharmaceutically active compounds suitable for the therapy and prophylaxis of cancer.

The compounds of formula (1), their pharmaceutically acceptable salts and/or derived forms, are further valuable pharmaceutically active compounds suitable for the therapy and prophylaxis of autoimmune diseases.

Accordingly, the invention also relates to a pharmaceutical composition comprising a compound of the invention and a pharmaceutically acceptable carrier or excipient.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The compounds of the invention may also be combined with sustained-release matrices, such as biodegradable polymers, to form therapeutic compositions.

In addition to the compounds of the invention, the pharmaceutical composition may further comprise and additional active ingredient for the treatment of the same disease as the compound of the invention or a different disease.

The composition of the invention preferably comprises a combination of a compound of the invention and an additional active ingredient for the treatment of a pain disorder and a pharmaceutically acceptable carrier.

The composition of the invention may further comprise a combination of a compound of the invention and an additional active ingredient for the treatment of cancer and a pharmaceutically acceptable carrier;

The composition of the invention may further comprise a combination of a compound of the invention and an additional active ingredient for the treatment of an autoimmune disease and a pharmaceutically acceptable carrier.

The active ingredients are for simultaneous or sequential administration.

The compounds of the invention may be administered by any suitable route.

Thus, a compound of the invention may be formulated as a pharmaceutical composition for oral, buccal, intranasal, parenteral (e. g. intravenous, intramuscular or subcutaneous), topical, or rectal administration or in a form suitable for administration by inhalation or insufflation.

For oral administration, the pharmaceutical composition may take the form of, for example, a tablet or capsule prepared by conventional means with a pharmaceutically acceptable excipient such as a binding agent (e. g., pregelatinized maize starch, polyvinylpyrrolidone or hydroxypropyl methylcellulose); filler (e. g., lactose, microcrystalline cellulose or calcium phosphate); lubricant (e. g., magnesium stearate, talc or silica); disintegrant (e. g., potato starch or sodium starch glycolate); or wetting agent (e. g., sodium lauryl sulphate). The tablets may be coated by methods well known in the art. Liquid preparations for oral administration may take the form of a, for example, solution, syrup or suspension, or they may be presented as a dry product for constitution with water or other suitable vehicle before use.

Such liquid preparations may be prepared by conventional means with a pharmaceutically acceptable additive such as a suspending agent (e. g., sorbitol syrup, methyl cellulose or hydrogenated edible fats); emulsifying agent (e. g., lecithin or acacia); non-aqueous vehicle (e. g., almond oil, oily esters or ethyl alcohol); and preservative (e. g., methyl or propyl p-hydroxybenzoates or sorbic acid).

For buccal administration, the composition may take the form of tablets or lozenges formulated in conventional manner. A compound of the present invention may also be formulated for sustained delivery according to methods well known to those of ordinary skill in the art.

Examples of such formulations can be found in U.S. Pat. Nos. 3,538,214, 4,060,598, 4,173,626, 3,119,742, and 3,492,397, which are herein incorporated by reference in their entirety.

A compound of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain a formulating agent such as a suspending, stabilizing and/or dispersing agent. Alternatively, the active ingredient may be in powder form for reconstitution with a suitable vehicle, e. g., sterile pyrogen-free water, before use parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The present invention further relates to a method of suppressing or alleviating a pain in a subject by administering a dose of an antagonist of the invention, and thereby modulating the activity of the FLT3 receptor.

The compounds of the present invention are therefore potentially useful in the treatment of a wide range of pain disorders, particularly acute pain, chronic pain, neuropathic pain, inflammatory pain, iatrogenic pain including cancer pain, infectious pain including herpetic pain visceral pain, central pain, dysfunctioning pain including fibromyalgia, nociceptive pain including post-surgical pain, and mixed pain types involving the viscera, gastrointestinal tract, cranial structures, musculoskeletal system, spine, urogenital system, cardiovascular system and CNS, including cancer pain, back and orofacial pain.

Other pain conditions that may be treated with the compounds of the present invention include autoimmune diseases including multiple sclerosis, neurodegenerative disorders, neurological disorders including epilepsy and sensomotor pathologies, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, causalgia, and conditions of lower urinary tract dysfunction.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain.

Moderate to severe acute nociceptive pain is a prominent feature of pain from central nervous system trauma, strains/sprains, burns, myocardial infarction and acute pancreatitis, postoperative pain (pain following any type of surgical procedure), posttraumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395).

Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenosis, polymyositis and pyomyositis;—heart and vascular pain, including pain caused by angina, myocardial infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders; and
orofacial pain, including dental pain, otic pain, burning mouth syndrome and temporomandibular myofascial pain.

The present invention further relates to a method of suppressing or alleviating cancer in a subject by administering a dose of an antagonist of the invention, and thereby modulating the activity of the FLT3 receptor.

The cancer is in particular acute myelogenous leukemia.

The present invention further relates to a method of suppressing or alleviating an autoimmune disease in a subject by administering a dose of an antagonist of the invention, and thereby modulating the activity of the FLT3 receptor.

The autoimmune disease includes but is not limited to the following: (1) a rheumatic disease such as rheumatoid arthritis, systemic lupus erythematosus, Sjogren's syndrome, scleroderma, mixed connective tissue disease, dermatomyositis, polymyositis, Reiter's syndrome or Behcet's disease (2) type II diabetes (3) an autoimmune disease of the thyroid, such as Hashimoto's thyroiditis or Graves' Disease (4) an autoimmune disease of the central nervous system, such as multiple sclerosis, myasthenia gravis, or encephalomyelitis (5) a variety of phemphigus, such as phemphigus vulgaris, phemphigus vegetans, phemphigus foliaceus, Senear-Usher syndrome, or Brazilian phemphigus, (6) psoriasis, and (7) inflammatory bowel disease (e.g., ulcerative colitis or Crohn's Disease).

Typically, a compound of the invention is administered in a therapeutically effective amount. By "therapeutically effective amount" is meant a sufficient amount of the antagonist of the invention to treat and/or to prevent the disease at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the disease being treated and the severity of the disease; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day. These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

The subject may be a human patient or an animal, preferably a mammal.

The following examples illustrate the preparation of the compounds of the formula (1) and their pharmacological properties

EXAMPLES

Example 1: Preparation of N-(5-chloro-2-hydroxyphenyl)-3-(piperidin-1-ylsulfonyl) benzamide 1—step 1: 3-(Piperidin-1-ylsulfonyl)benzoic Acid To a stirred solution of 3-(chlorosulfonyl) benzoic acid (0.3 g, 1.36 mmol) in DCM (5 mL) was added piperidine (0.35 g, 0.4 ml, 4.08 mmol) at 0° C., and the resulting solution was stirred for 2 hours. The volatiles were then evaporated under reduced pressure and the residue treated with aqueous 1N $KHSO_4$. The aqueous phase was then extracted with ethyl acetate (×3), and the combined organic phases dried over anhydrous magnesium sulfate, filtered and evaporated in vacuo to give 3-(piperidin-1-ylsulfonyl)benzoic acid as a white solid (0.34 g, 1.262 mmol, 90%). $^1$H NMR (400 MHZ, $CDCL_3$): 8.41 (1H, br), 8.26 (1H, dt, J=8.0 Hz, 1.4 Hz), 7.94 (1H, dt, J=8.0 Hz, 1.6 Hz), 7.61 (1H, t, J=7.7 Hz), 2.98-2.96 (4H, m), 1.62-1.56 (4H, m), 1.40-1.34 (2H, m).

$^{13}$C NMR (100 MHz, CDCl$_3$): 170.0, 137.6, 133.9, 132.5, 130.3, 129.4, 129.2, 46.9, 25.2, 23.5.

2-Step 2: N-(5-chloro-2-hydroxyphenyl)-3-(piperidin-1-ylsulfonyl) benzamide

To a stirred solution of 3-(Piperidin-1-ylsulfonyl) benzoic acid (0.15 g, 0.557 mmol) in DCM (3.15 ml) was added (Benzotriazol-1-yloxy)tris(dimethylamino)phosphonium hexafluorophosphate (BOP, 0.29 g, 0.668 mmol), N-Methyl morpholine (0.14 g, 1.39 mmol) at RT, and the resulting solution was stirred for 15 min. 5-chloro-2-hydroxyaniline (0.080 g, 0.557 mmol) was then added and the final mixture was stirred at RT for 12 hours. The solvent was then evaporated under reduced pressure, the residue taken into Ethyl acetate (15 ml) and washed with HCl 1N (8 ml), KHCO3 1N (8 ml), water (10 ml). The organic layer was dried (Na$_2$SO$_4$), filtered and concentrated under reduce pressure. The resulting residue was purified by silica gel flash chromatography (AcOEt/hept 3/7) to afford N-(5-chloro-2-hydroxyphenyl)-3-(piperidin-1-ylsulfonyl) benzamide as a white solid (160 mg, 73%).

$^1$H NMR (400): 8.70 (s, H), 8.19 (1H, t, J=1.6 Hz), 8.12 (1H, dt, J=1.6 Hz, 8 Hz), 7.85 (1H, dt, J=1.6 Hz, 8 Hz), 7.62 (t, 1h, 8 Hz), 7.48 (d, 1H, J=2.4 Hz), 7.03 (dd, 1H, J=2.4 Hz, J=8.8 Hz); 8.90 (d, 1H, J=8.8 Hz)

$^{13}$C NMR (100 MHz, CDCl$_3$): 166.5, 146.9, 137.3, 134.4, 132.1, 131.1, 129.9, 126.9, 126.5, 126.1, 125.5, 122.5, 120.0, 47.0, 25.05, 23.3.

LC/MS (M+H)=395.8

Example 2: Preparation of N-(5-chloro-1H-indol-7-yl)-3-(piperidin-1-ylsulfonyl)benzamide 7-bromo-4-chloro-1H-indole To a stirred solution of 1-bromo-4chloro-2-nitrobenzene (1.3 g, 5.49 mmol) in THF (28 ml) was added vinylmagnesium bromide (1M in THF, 16.5 ml, 123 mmol) at −45° C. and the reaction mixture was stirred at the same temperature for 1 hour. Then the reaction mixture was quenched with saturated NH$_4$Cl (20 ml). The volatile components were evaporated under reduced pressure and H$_2$O (30 ml) was added to the resulting residue. The crude was extracted with DCM (2×15 ml) and the organic layer was washed with brine (50 ml) dried over Na$_2$SO$_4$ and concentrated in vacuo. The residue was purified by flash chromatography using AcOEt/Heptane (1/19) to give the title compound as a yellow oil (0.6 g, 47%)

$^1$H NMR (400 MHZ, CDCl$_3$): 8.35 (s, 1H, br), 7.22 (t, 1H, J=2.8 Hz), 7.17 (d, 1H, J=8 Hz) 6.94 (d, J=8 Hz, 1H), 6.66 (t, 1H, J=2.8 Hz)

$^{13}$C NMR (100 MHz, CDCl$_3$): 135.0, 127.5, 125.6, 125.2, 124.7, 120.7, 102.8 tert-butyl 7-bromo-4-chloro-1H-indole-1-carboxylate

Under argon, 60% NaH dispersion in mineral oil (130 mg, 5.42 mmol) was added in portions to 7-bromo-4-chloro-1H-indole (500 mg, 2.17 mmol) in THF (9 mL) at 0° C. After gas evolution ceased, a solution of Boc$_2$O (660 m g, 3 mmol) in THF (2 mL) was added dropwise. The reaction was stirred overnight at room temperature and worked up by slow addition of H$_2$O (15 ml). The reaction mixture was extracted with Et$_2$O (3×10 ml) and the combined organic layers were washed with brine and dried over Na$_2$SO$_4$. The solvent was removed under vacuum and the oily protected indole was taken into the next step without further purification (550 mg, 77%).

$^1$H NMR (400 MHZ, CDCl$_3$): 7.47 (d, 1H J=3.6 Hz), 7.36 (d, 1H, J=8.4 Hz), 7.03 (d, 1H, J=8.4 Hz), 6.62 (d, 1H J=3.6 Hz), 1.47 (s, 9H).

$^{13}$C NMR (100 MHz, CDCl$_3$): 148.1, 141.4, 132.4, 130.7, 130.12, 129.9, 123.7, 105.9, 105.2, 84.9, 29.7, 27.9

3-(piperidine-1-sulfonyl)benzamide

To a solution of 3-(Piperidin-1-ylsulfonyl) benzoic Acid (300 mg, 1.11 mmol) in AcOEt (5 mL) was added N,N-carbonyldiimidazole (198 mg, 1.22 mmol). The reaction mixture was allowed to stir at reflux for 4 hours and then ammonium acetate (343.5 mg, 4.46 mmol) was added. The reaction mixture was allowed to stir at reflux overnight and then the volatile components were evaporated under reduced pressure. The residue was further purified by flash chromatography using AcOEt/Heptane to give the title compound as a white solid (240 mg, 80%).

$^1$H NMR (400, CDCl$_3$): 8.10 (t, 1H, J=2 Hz), 8.03 (dt, 1H, J=2 Hz, 8 Hz), 7.84 (dt, 1H, J=2 Hz, 8 Hz), 7.57 (t, 1H, J=8 Hz), 6.36 (s, 1H, br), 5.94 (s, 1H, br).

$^{13}$C NMR (100 MHz, CDCl$_3$) 167.6, 137.2, 134.5, 134.8, 130.7, 129.6, 46.9, 25.14, 23.4

N-(5-chloro-1H-indol-7-yl)-3-(piperidin-1-ylsulfonyl)benzamide

A 5 ml microwave vial (oven-dried and under nitrogen) containing a Teflon® stirred bar was charged with the corresponding 3-(piperidine-1-sulfonyl)benzamide (80 mg, 0.29 mmol), tert-butyl 7-bromo-5-chloro-1H-indole-1-carboxylate (98.57 mg, 0.29 mmol), Cs$_2$CO$_3$ (194.3 mg, 0.59 mmol) followed by the addition of anhydrous dioxanne (1.23 ml). The mixture vessel was evacuated and backfilled with nitrogen (this process was repeated a total of 3 times) and then Pd(OAc)$_2$ (2.0 mg, 0.009 mmol) and Xantphos (10.35 mg, 0.017 mmol) were added. The reaction mixture was then capped properly and placed in a preheated oil bath at 105° C. until complete conversion of the starting material (3 hours). After filtration through a pad of Celite® the solvent was evaporated in vacuo. The reaction mixture was extracted with AcOEt (3×10 ml) and the combined organic layers were washed with brine and dried over Na$_2$SO$_4$. The crude product was purified by chromatography on silica gel using AcOEt/Hept (1/4) to give the expected product as a white solid.

$^1$H NMR (400 MHZ, DMSO-d6): 11.3 (s, 1H, br), 10.5 (s, 1H, br), 8.38-8.35 (m, 2H), 7.97 (d, 1H, J=7.6 Hz), 7.84 (t, 1H, J=7.6 Hz), 7.49 (s, 1H), 7.26 (d, 1H, J=8 Hz), 7.10 (d, 1H, J=8 Hz), 6.52 (s, 1H), 2.96 (m, 4H), 1.57 (m, 4H), 1.38 (m, 2H)

$^{13}$C NMR (100 MHz, DMSO-d6): 164.4, 136.0, 135.6, 132.3, 130.9, 130.2, 129.6, 130, 2, 127.3, 126.7, 126.5, 121.9, 121.4, 118.2, 117.3, 99.8, 46.6, 24.7, 22.9

LC/MS (M+H)=420.9

Example 3: Preparation of N-(2-chlorophenyl)-3-(piperidin-1-ylsulfonyl)benzamide 2-Chloro aniline (62.9 mg, 0.675 mmol) was dissolved in CH$_2$Cl$_2$ (1 mL), followed by addition of DIEA (117 μL, 0.675 mmol) at 0° C. Then, m-(chlorosulfonyl)benzoyl chloride (113.36 μL, 0.743 mmol) in a solution of CH$_2$Cl$_2$ (1 mL) was added to the reaction mixture by syringe, dropwise. After reacting for 30 min, the ice bath was removed. DIEA (117 µL, 0.675 mmol), DMAP (6.81 mg, 0.0675 mmol), piperidine (66 µL, 0.675 mmol) were added to the solution at 25° C. The reaction was checked by TLC until the starting material was completely converted to product (1 h). After removal of $CH_2Cl_2$ under reduced pressure, the crude mixture was purified by column chromatography to obtain the desired product (40%).

White solid; mp: 150-151° C.; $^1$H NMR (300 MHz, DMSO-$d_6$): δ 10.52 (s, 1H), 8.29 (d, J=6 Hz, 2H), 7.93 (d, J=9 Hz), 7.84-7.77 (m, 3H), 7.38 (t, J=6 Hz, 2H), 7.13 (t, J=6 Hz, 1H), 2.93 (t, J=6 Hz, 4H), 1.58-1.50 (m, 4H), 1.37-1.32 (m, 2H); $^{13}$C NMR (75 MHz, DMSO-$d_6$): δ 164.0, 138.7, 136.0, 135.9, 132.0, 130.1, 129.6, 128.6, 126.4, 124.0, 120.6, 46.6, 24.6, 22.8; HRMS (ESI): calcd for $C_{18}H_{20}N_2O_3S$ [M–H]$^-$: 343.1116, found: 343.1108;

Example 4: Preparation of 4-chloro-2-(5-(3-(piperidin-1-ylsulfonyl)phenyl)-4H-1,2,4-triazol-3-yl)phenol Methyl 3-(piperidin-1-ylsulfonyl)benzoate To a stirred solution of 3-Chlorosulfonyl methyl benzoate (300 mg, 1.28 mmol) in DCM (10 mL), piperidine (3.84 mol, 3 eq) was added dropwise under ice cooling and the mixture was stirred for 2 hours. HCl 1N (8 ml) was added thereto. After separation, the organic phase was washed with brine (8 mL) and dried ($Na_2SO_4$). The solvent was evaporated and the resulting compound was used directly without further purification. (Yield=91%).

$^1$H NMR (400 MHZ, CDCl$_3$): 8.37 (1H, s), 8.24 (2H, dd), 7.92 (1H, d), 7.60 (1H, t), 2.99 (1H, m), 1.64 (4H, m), 1.41 (2H, m).

3-(piperidin-1-ylsulfonyl)benzohydrazide

To a solution of the Methyl 3-(piperidin-1-ylsulfonyl) benzoate (160 mg, 0.56 mmol) in MeOH (0.5 ml) was added hydrazine (1.12 mmol, 2 eq). The mixture was stirred at room temperature for 1 night. After removal of the solvent the crude product was triturated with Et$_2$O, the precipitated crystals were filtered off. Resulting compound was used directly without further purification. (Yield=81%).

$^1$H NMR (400 MHZ, CDCl$_3$): 8.12 (2H, m), 7.85 (1H, d), 7.72 (1H, t), 2.88 (4H, m), 1.53 (4H, m), 1.34 (2H, m).

5-chloro-2-methoxybenzonitrile

To a suspension of commercially available 5-chloro-2-hydroxybenzonitrile (200 mg, 1.3 mmol) and powder potassium carbonate (0.5 g, 3.9 mmol) in DMF (4 mL) was added methyl iodide (0.12 mL, 1.93 mmol, 1.5 eq) and the mixture was stirred at room temperature for 1 night. Et$_2$O (20 mL) was added and the resulting organic phase was washed with HCL 1N (15 mL), water (15 mL) and dried ($Na_2SO_4$). The solvent was evaporated and the resulting benzonitrile derivative was used directly without further purification. (Yield 94%).

$^1$H NMR (400 MHZ, CDCl$_3$): 7.49 (1H, d), 7.46 (1H, d), 6.89 (1H, d), 3.90 (3H, s).

5-chloro-2-methoxybenzimidamide

To a solution of 5-chloro-2-methoxybenzonitrile (50 mg, 0.30 mmol) in anhydrous THF (1 mL) was added dropwise a solution of Lithium hexamethyldisilazane (5 eq of 1 M solution in THF) at rt. The reaction mixture was stirred for 48 h and then acidified to pH=3 with HCl 1N. The solvent was removed and the solution was basified to pH=12 with NaOH 2 N. The product was extracted with DCM, the organic layer was dried ($Na_2SO_4$) and the solvent was removed (Yield 87%).

$^1$H NMR (400 MHZ, CDCl$_3$): 7.52 (1H, d), 7.27 (1H, d), 6.83 (1H, d), 5.70 (2H, NH), 3.82 (3H, s).

1-(3-(5-(5-chloro-2-methoxyphenyl)-4H-1,2,4-triazol-yl)phenylsulfonyl)piperidine To a solution of 3-(piperidin-1-ylsulfonyl)benzohydrazide (61.4 mg, 0.22 mmol) in EtOH (1 ml) was added (40 mg, 0.22 mmol) and the resulting mixture was stirred under reflux for 6 hours. Bromobenzene (1 ml) was then added 5-chloro-2-methoxybenzimidamide and the mixture was stirred one night at 105° C. The solvents were removed under vacuum and the crude was purified by flash chromatography (inverse phase MeOH/Water) (Yield=41%).

$^1$H NMR (400 MHZ, CDCl$_3$): 8.44 (1H, s), 8.36 (1H, dd), 7.98 (1H, s), 7.92 (1H, dd), 7.70 (1H, t), 7.48 (1H, dd), 7.01 (1H, d), 3.97 (3H, s), 3.05 (4H, m), 1.65 (4H, m), 1.43 (2H, m).

4-chloro-2-(5-(3-(piperidin-1-ylsulfonyl)phenyl)-4H-1,2,4-triazol-3-yl)phenol

To a solution of 1-(3-(5-(5-chloro-2-methoxyphenyl)-4H-1,2,4-triazol-yl)phenylsulfonyl)piperidine (45 mg, 0.1 mmol) in DCM (1 mL) at –78° C. was added BBr$_3$ (5 eq). The resulting solution was stirred 1 hour at –78° C., and 2 h at room temperature. After neutralization with MeOH, the solvents were removed. The crude was purified by flash chromatography (inverse phase MeOH/Water) to obtain the final product (Yield=55%).

$^1$H NMR (400 MHZ, MeOD): 8.49-8.39 (2H, m), 8.04-7.76 (3H, m), 7.98 (1H, s), 7.48-7.34 (1H, dd), 7.10-7.02 (1H, dd), 3.06 (4H, m), 1.66 (4H, m), 1.46 (2H, m).

LC-MS ESI [M+H]$^+$=418.8

Example 5: Preparation of 4-chloro-2-(2-(3-(piperidin-1-ylsulfonyl)phenyl)-1H-imidazol-5-yl)phenol 1-(5-chloro-2-methoxyphenyl)ethanone To a suspension of commercially available 5-chloro-2-hydroxyphenyl)ethanone (200 mg, 1.17 mmol) and powder potassium carbonate (0.5 g, 3.9 mmol) in acetone (2 mL) was added methyl iodide (0.10 mL, 1.75 mmol, 1.5 eq) and the mixture was stirred at room temperature for 1 night. Et$_2$O (20 mL) was added and the resulting organic phase was washed with HCL 1N (15 mL), water (15 mL) and dried ($Na_2SO_4$). The solvent was evaporated and the resulting benzonitrile derivative 3 was used directly without further purification. (Yield 79%).

$^1$H NMR (400 MHZ, CDCl$_3$): 7.66 (1H, d), 7.38 (1H, dd), 6.88 (1H, dd), 3.88 (3H, s), 2.57 (3H, s).

2-bromo-1-(5-chloro-2-methoxyphenyl)ethanone

To a solution of 1-(5-chloro-2-methoxyphenyl)ethanone (100 mg, 0.542 mmol) in DCM CHCl$_3$ (1 ml) was added bromine (0.029 ml, 0.57 mmol) dropwise and the resulting mixture was stirred at RT until completion of the reaction on TLC plate (2 h). The organic phase was washed with water, brine, dried $Na_2SO_4$) and evaporated under vacuum. The resulting bromo ethanone derivative was used directly without further purification. (Yield 95%).

¹H NMR (400 MHZ, CDCl₃): 7.76 (1H, d), 7.44 (1H, dd), 6.91 (1H, dd), 4.53 (2H, s), 3.90 (3H, s).

3-(piperidin-1-ylsulfonyl)benzoic acid

To a stirred solution of the commercially available 3-(chlorosulfonyl) benzoic acid 9 (0.3 g, 1.36 mmol) in DCM (5 mL) was added piperidine (0.35 g, 0.4 ml, 4.08 mmol) at 0° C., and the resulting solution was stirred for 2 hours. The volatiles were then evaporated under reduced pressure and the residue treated with aqueous 1N KHSO₄. The aqueous phase was then extracted with ethyl acetate (×3), and the combined organic phases dried over anhydrous magnesium sulfate, filtered and evaporated in vacuo to give 3-(piperidin-1-ylsulfonyl)benzoic acid as a white solid (0.34 g, 1.262 mmol, 90%).

¹H NMR (400 MHZ, CDCl₃): 8.41 (1H, br), 8.26 (1H, dt, J=8.0 Hz, 1.4 Hz), 7.94 (1H, dt, J=8.0 Hz, 1.6 Hz), 7.61 (1H, t, J=7.7 Hz), 2.98-2.96 (4H, m), 1.62-1.56 (4H, m), 1.40-1.34 (2H, m).

¹³C NMR (100 MHz, CDCl₃): 170.0, 137.6, 133.9, 132.5, 130.3, 129.4, 129.2, 46.9, 25.2, 23.5.

3-(piperidin-1-ylsulfonyl)benzamide

To a solution of 3-(piperidin-1-ylsulfonyl)benzoic acid (300 mg, 1.11 mmol), in DMF (5 mL) and at 4° C. were added DIEA (0.74 mL, 4.45 mmol), HATU (466 mg, 1.22 mg) and NH₄Cl, 120 mg, 2.23 mmol). After removal of the ice bath, the resulting solution was stirred overnight at RT. The volatile were then evaporated under vacuum, and to the resulting crude, AcOEt was added (30 mL). The organic layer was washed with HCl 1N, water, brine and finally dried (Na₂SO₄). The solvent was removed under vacuum, and resulting compound 7 was used directly without further purification. (Yield=74%).

¹H NMR (400 MHZ, CDCl₃): 8.14 (1H, s), 8.05 (2H, dd), 7.89 (1H, d), 7.62 (1H, t), 6.26 (1H, NH), 5.85 (1H, NH), 2.99 (4H, m), 1.63 (4H, m), 1.40 (2H, m).

3-(piperidin-1-ylsulfonyl)benzonitrile

To a solution of 3-(piperidin-1-ylsulfonyl)benzamide (220 mg, 0.82 mmol) was added POCl₃ (2 mL) and the resulting mixture was stirred at 90° C. for 35 min. The excess of POCL₃ was then evaporated under vacuum and the crude was added into ice-water dropwise with stirring. After neutralization of the solution (pH=7) with NaOH 2N, the product was extracted twice with AcOEt.). The organic layer was washed with water, brine and finally dried (Na₂SO₄). The solvent was removed under vacuum, and the resulting benzonitrile was used directly without further purification. (Yield=95%).

¹H NMR (400 MHZ, CDCl₃): 8.02 (1H, s), 7.95 (2H, dd), 7.85 (1H, d), 7.65 (1H, t), 3.00 (4H, m), 1.64 (4H, m), 1.43 (2H, m).

3-(piperidin-1-ylsulfonyl)benzimidamide

To a solution of 3-(piperidin-1-ylsulfonyl)benzonitrile (195 mg, 0.78 mmol) in anhydrous THF (2 mL) was added dropwise a solution of Lithium hexamethyldisilazane (2.6 eq, 1 M solution in THF) at rt. The reaction mixture was stirred for 10 h and then acidified to pH=3 with HCl 1N. The solvent was removed and the solution was basified to pH=12 with NaOH 2 N. The product was extracted with DCM, the organic layer was dried (Na₂SO₄) and the solvent was removed (Yield 60%).

¹H NMR (400 MHZ, CDCl₃): 8.15-7.80 (3H, m), 7.60 (1H, m), 4.41 (3H, NH), 2.97 (4H, m), 1.60 (4H, m), 1.39 (2H, m).

5-(5-chloro-2-methoxyphenyl)-2-(3-(piperidin-1-ylsulfonyl)phenyl)-1H-imidazole

To a solution of 3-(piperidin-1-ylsulfonyl)benzimidamide (51 mg, 0.19 mmol) in THF (0.88 mL) and H₂O (1 mL) was added NaHCO3 (64 mg, 0.76 mmol). The reaction mixture was than heated under reflux for 20 min. Then, a solution of 2-bromo-1-(5-chloro-2-methoxyphenyl)ethanone (50 mg, 0.19 mmol) was added and reflux was extended for an additional 2 hours. The flask was removed from the oil bath, cooled to RT and the volatiles were evaporated under vacuum. The crude was than dissolved into AcOEt (15 ml), and the organic layer was washed with water, brine, dried ((Na₂SO₄) and the solvent was removed. (Yield=92%).

¹H NMR (400 MHZ, CDCl₃): 8.26 (1H, d), 8.17 (1H, s), 7.75-7.67 (4H, m), 7.18 (1H, dd), 6.90 (1H, d), 3.94 (3H, s), 3.05-2.95 (4H, m), 1.59 (4H, m), 1.38 (2H, m).

4-chloro-2-(2-(3-(piperidin-1-ylsulfonyl)phenyl)-1H-imidazol-5-yl)phenol

To a solution of 5-(5-chloro-2-methoxyphenyl)-2-(3-(piperidin-1-ylsulfonyl)phenyl)-1H-imidazole (75 mg, 0.17 mmol) in DCM (1 mL) at −78° C. was added BBr₃ (5 eq). The resulting solution was stirred 1 hour at −78° C., and 2 h at room temperature. After neutralization with MeOH, the solvents were removed. The crude was purified by flash chromatography (inverse phase MeOH/Water) to obtain the final product (Yield=30%).

¹H NMR (400 MHZ, CDCl₃): 8.27 (1H, s), 8.11 (1H, d), 7.75 (1H, d), 7.60 (1H, t), 7.52 (1H, s), 7.44 (1H, s), 6.77-6.70 (2H, m), 2.99 (4H, m), 1.60 (4H, m), 1.39 (2H, m).

¹³C NMR (400 MHz, CD₃OD): 153.3, 139.2, 131.4, 130.0, 129.8, 129.7, 126.8, 126.0, 125.4, 119.0, 118.7, 48.5, 26.5, 24.6.

LC-MS ESI [M+H]⁺=418.0

Example 6: Preparation of 2-3(piperidin-1ylsulfonyl)phenylbenzo[d]oxazole 3-(Piperidin-1-ylsulfonyl)benzoic acid To a stirred solution of 3-(chlorosulfonyl) benzoic acid (0.3 g, 1.36 mmol) in DCM (5 mL) was added piperidine (0.35 g, 0.4 ml, 4.08 mmol) at 0° C., and the resulting solution was stirred for 2 hours. The volatiles were then evaporated under reduced pressure and the residue treated with aqueous 1N KHSO₄. The aqueous phase was then extracted with ethyl acetate (×3), and the combined organic phases dried over anhydrous magnesium sulfate, filtered and evaporated in vacuo to give 3-(piperidin-1-ylsulfonyl)benzoic acid as a white solid (0.34 g, 1.262 mmol, 90%).

¹H NMR (400 MHZ, CDCl₃): 8.41 (1H, br), 8.26 (1H, dt, J=8.0 Hz, 1.4 Hz), 7.94 (1H, dt, J=8.0 Hz, 1.6 Hz), 7.61 (1H, t, J=7.7 Hz), 2.98-2.96 (4H, m), 1.62-1.56 (4H, m), 1.40-1.34 (2H, m).

¹³C NMR (100 MHz, CDCl₃): 170.0, 137.6, 133.9, 132.5, 130.3, 129.4, 129.2, 46.9, 25.2, 23.5.

N-(5-chloro-2-hydroxyphenyl)-3-(piperidin-1-ylsulfonyl) benzamide

To a stirred solution of 3-(Piperidin-1-ylsulfonyl) benzoic acid (0.15 g, 0.557 mmol) in DCM (3.15 ml) was added (Benzotriazol-1-yloxy)tris(dimethylamino)phosphonium hexafluorophosphate (BOP, 0.29 g, 0.668 mmol), N-Methyl morpholine (0.14 g, 1.39 mmol) at RT, and the resulting solution was stirred for 15 min. 5-chloro-2-hydroxyaniline (0.080 g, 0.557 mmol) was then added and the final mixture was stirred at RT for 12 hours. The solvent was then evaporated under reduced pressure, the residue taken into Ethyl acetate (15 ml) and washed with HCl 1N (8 ml), KHCO3 1N (8 ml), water (10 ml). The organic layer was dried ($Na_2SO_4$), filtered and concentrated under reduce pressure. The resulting residue was purified by silica gel flash chromatography (AcOEt/hept 3/7) to afford N-(5-chloro-2-hydroxyphenyl)-3-(piperidin-1-ylsulfonyl) benzamide as a white solid (160 mg, 73%).

$^1$H NMR (400 MHZ, $CDCl_3$): 8.70 (s, H), 8.19 (1H, t, J=1.6 Hz), 8.12 (1H, dt, J=1.6 Hz, 8 Hz), 7.85 (1H, dt, J=1.6 Hz, 8 Hz), 7.62 (t, 1h, 8 Hz), 7.48 (d, 1H, J=2.4 Hz), 7.03 (dd, 1H, J=2.4 Hz, J=8.8 Hz); 8.90 (d, 1H, J=8.8 Hz)

$^{13}$C NMR (100 MHz, $CDCl_3$): 166.5, 146.9, 137.3, 134.4, 132.1, 131.1, 129.9, 126.9, 126.5, 126.1, 125.5, 122.5, 120.0, 47.0, 25.05, 23.3.

2-3(piperidin-1ylsulfonyl)phenylbenzo[d]oxazole

A 5 ml microwave vial (oven-dried and under nitrogen) containing a Teflon® stirred bar was charged with N-(5-chloro-2-hydroxyphenyl)-3-(piperidin-1-ylsulfonyl) benzamide (10 mg, 0.025 mmol.) followed by the addition of TFA (0.1 ml) and AcOH (0.1 ml). The reaction mixture was then capped properly and heated at 100° C. under microwave irradiations for 90 min. TFA was removed and the crude product was purified by LC inverse phase (MeOH/$H_2O$ 5/95 to 95/5) (Yield=42%).

$^1$H NMR (400 MHZ, DMSO): 8.50 (1H, dd), 8.41 (1H, d), 8.00 (2H, m), 7.91 (2H, m), 7.53 (1H, d), 2.96 (4H, m), 1.55 (4H, m), 1.37 (2H, m).

LC-MS ESI [M+H]$^+$=376.8

Example 7: Preparation of N-(3-aminopropyl)-3-(5-chloro-1,3-benzoxazol-2-yl)-N-cyclohexylbenzene-1-sulfonamide

Methyl-3-(cyclohexylsulfamoyl)benzoate

To a stirred solution of the commercially available 3-chlorosulfonyl methyl benzoate (1012 mg, 4.13 mmol) in DCM (10 mL) was added cyclohexylamine (855 mg, 099 ml, 8.26 mmol) dropwise and the resulting solution was stirred at 4° C. for 2 hours. The organic layer was washed with HCl 1N, brine and dried ($Na_2SO_4$). The solvent was removed and the product was used without further purification (Yield=94%).

$^1$H NMR (400 MHZ, $CDCl_3$): 8.52 (1H, s), 8.20 (2H, d), 8.06 (1H, d), 7.57 (1H, t), 3.92 (3H, s), 3.14 (1H, m), 1.70 (2H, m), 1.60 (2H, m), 1.24-1.05 (5H, m).

Methyl-3-(N-((tert-butoxycarbonyl)amino)propyl)-N-cyclohexylsulfamoyl)benzoate To a suspension of the above-prepared methyl-3-(cyclohexylsulfamoyl)benzoate (500 mg, 1.68 mmol) and powder potassium carbonate (975 mg, 7.06 mmol) in DMF (5 mL) were added TBAB (27.1 mg, 0.085 mmol) and commercially available tert-butyl N-(3-chloropropyl)carbamate (423 mg, 2.18 mmol). The resulting mixture was stirred overnight at 70° C.

The solvent was removed and AcOEt was added. The organic layer was washed with HCl 1N, water, brine, dried ($Na_2SO_4$) and the solvent was evaporated. The crude was purified by chromatography on silica gel Hept/AcOEt 90/10 to 70/30 (Yield=67%).

$^1$H NMR (400 MHZ, $CDCl_3$): 8.40 (1H, s), 8.15 (2H, d), 7.95 (1H, d), 7.53 (1H, t), 4.91 (1H, NH), 3.90 (3H, s), 3.56 (1H, m), 3.16 (4H, m), 1.77 (2H, m), 1.67 (2H, m), 1.50 (4H, m), 1.39 (9H, s), 1.26 (5H, m), 0.97 (1H, m).

3-[(3-{[(tert-butoxy)carbonyl]amino}propyl)(cyclohexyl)sulfamoyl]benzoic acid Methyl-3-(N-((tert-butoxycarbonyl)amino)propyl)-N-cyclohexylsulfamoyl)benzoate (510 mg, 1.12 mmol) was dissolved in a mixture MeOH (10 ml) and $H_2O$ (8 ml). NaOH (5 eq, 5.60 mmol) was added and the resulting mixture was stirred overnight at RT. After evaporation of the methanol, the aqueous layer was extracted with AcOEt (8 ml). The aqueous layer was then neutralized with HCl 1N and extracted twice with AcOEt. The organic phase was dried ($Na_2SO_4$) and the solvent was evaporated. (Yield 85%).

$^1$H NMR (400 MHZ, $CDCl_3$): 8.49 (1H, s), 8.23 (1H, dd), 8.01 (1H, d), 7.57 (1H, t), 4.96 (1H, m), 3.58 (1H, m), 3.21 (4H, m), 1.82-0.95 (21H, m).

Tert-butyl N-[3-(N-cyclohexyl{3-[(5-chloro-2-hydroxyphenyl)-carbamoyl]-phenyl}-sulfonamido)-propyl]carbamate To a solution of the above-mentioned 3-[(3-{[(tert-butoxy)carbonyl]amino}propyl)(cyclohexyl)sulfamoyl]benzoic acid (100 mg, 0.23 mmol), in DMF (2 mL) and at 4° C. were added DIEA (0.075 mL, 0.45 mmol), HATU (95 mg, 0.25 mmol) and 5-chloro-2-hydroxyaniline (32.6 mg, 0.23 mmol). After removal of the ice bath, the resulting solution was stirred 45 min at RT. The volatile were then evaporated under vacuum, and to the resulting crude, AcOEt was added (30 mL). The organic layer was washed with HCl 1N, water, brine and finally dried ($Na_2SO_4$). The solvent was removed under vacuum, and resulting compound was purified chromatography on silica gel with Hept/AcOEt 90/10 to 60/40 (Yield 45%).

$^1$H NMR (400 MHZ, $CDCl_3$): 8.56 (1H, s), 8.33 (1H, d), 8.04 (1H, d), 7.63 (1H, t), 6.99 (1H, d), 6.81 (1H, s), 6.73 (1H, m), 4.87 (1H, m), 3.61 (1H, m), 3.18 (4H, m), 1.80-0.80 (21H, m).

N-(3-aminopropyl)-3-(5-chloro-1,3-benzoxazol-2-yl)-N-cyclohexylbenzene-1-sulfonamide A 5 ml microwave vial (oven-dried and under nitrogen) containing a Teflon® stirred bar was charged with the above compound Tert-butyl N-[3-(N-cyclohexyl{3-[(5-chloro-2-hydroxyphenyl)-carbamoyl]-phenyl}-sulfonamido)-propyl]carbamate (20 mg, 0.035 mmol.) followed by the addition of TFA (0.3 ml). The reaction mixture was then capped properly and heated at 90° C. under microwave irradiations for 90 min. TFA was removed and the crude product was purified by LC inverse phase (MeOH/$H_2O$ 5/95 to 95/5) (Yield=95%).

$^1$H NMR (400 MHZ, MeOD): 8.65 (1H, s), 8.46 (1H, d), 8.09 (1H, d), 7.79 (2H, m), 7.70 (1H, d), 7.45 (1H, d), 3.70

(1H, m), 3.39 (2H, m), 3.07 (2H, m), 2.03 (2H, m), 1.72 (2H, m), 1.61-1.25 (7H, m), 1.08 (1H, m).

$^{13}$C NMR (400 MHz, CD$_3$OD): 164.3, 151.0, 144.1, 143.8, 132.6, 131.8, 131.2, 129.1, 127.6, 127.0, 121.0, 113.2, 60.1, 42.2, 38.4, 32.9, 31.0, 27.2, 26.3.

LC-MS ESI [M+H]$^+$=448.0

Example 8: Preparation of 2-[3-(1-piperidylsulfonyl)phenyl]-3H-benzimidazol-4-ol 4-(piperidin-1-ylsulfonyl)phenyl)methanol 3-(piperidin-1-ylsulfonyl)benzoic acid (100 mg, 0.37 mmol) was dissolved in DME (2 mL) and cooled in an ice bath. N-methyl morpholine (0.042 ml, 0.39 mmol) and i-Bu-chloroformate (0.050 ml, 0.39 mmol) were then added, the mixture was stirred at 0° C. for 10 min. A solution of NaBH$_4$ (56 mg, 1.45 mmol) in water (1 ml) was added, and stirring was continued for 1 h at RT. Excess of NaBH$_4$ was quenched by a slow addition of HCl1N AcOEt (15 mL) ware added, and the phases were separated. The organic layer was washed with water, dried over sodium sulfate, filtered and concentrated (yield: 100%)

$^1$H NMR (400 MHZ, CDCl$_3$): 7.77 (1H, s), 7.69 (1H, d), 7.62 (1H, d), 7.54 (1H, t), 4.81 (2H, s), 1.65 (4H, m), 1.43 (2H, m).

4-(piperidin-1-ylsulfonyl)benzaldehyde

In round-bottom flask oxalyl chloride (freshly distilled, d=1.455, 0.045 ml, 0.53 mmol) was dissolved in 1.8 mL of dry DCM (dried over CaH$_2$). The solution was cooled to −78° C. and a solution of dry dimethylsulfoxide (0.05 mL, 0.7 mmol) in 0.5 mL of dry DCM was slowly added under argon. The internal temperature during the addition was kept below −70° C. After complete addition, the mixture was stirred for 15 min at −78° C. and a solution of 4-(piperidin-1-ylsulfonyl)phenyl)methanol in 0.3 ml of dry DCM was slowly added. After stirring the reaction mixture for 45 min at −78° C., NEt$_3$ (d=0.726, 0.2 ml, 1.4 mmol) was slowly added and the reaction mixture was maintained for 45 min at −78° C. and then the cooling bath was removed and after warming to room temperature, the suspension was treated with 150 mL of saturated NaHCO3 solution.

The layers were separated and the organic layer was washed with saturated aqueous NaHCO3 (2×) and with brine (1×). After drying over Na2SO4 (1 h stirring), solvent was evaporated to yield the crude aldehyde as a white solid which was used without further purification. (Yield: 73 mg, 82%)

1H NMR (400 MHZ, CDCl3): 10.06 (1H, s), 8.20 (1H, s), 8.07 (1H, d), 7.98 (1H, d), 7.69 (1H, t), 3.00 (2H, s), 1.62 (4H, m), 1.40 (2H, m).

2-[3-(1-piperidylsulfonyl)phenyl]-3H-benzimidazol-4-ol

To a solution of the above-mentioned 4-(piperidin-1-ylsulfonyl)benzaldehyde (30 mg, 0.12 mmol) in a mixture of EtOH (1 ml) and H$_2$O (0.1 ml) were added Na$_2$S$_2$O$_5$ (0.4 mg, 0.002 mmol) and 2,3-diamino phenol (obtained by catalytic hydrogenation of commercially available 2-amino-3-nitrophenol, 16.1 mg, 0.13 mmol)). The resulting mixture was refluxed for 6 h, the solvents were removed AcOEt (10 mL) was added and the resulting organic phase was washed with, water (8 mL) and dried (Na$_2$SO$_4$). The solvent was evaporated. The crude was purified by flash chromatography (inverse phase MeOH/Water) to obtain the final product (Yield=76%).

$^1$H NMR (400 MHZ, CD$_3$OD): 8.51 (1H, s), 8.37 (1H, d), 8.04 (1H, d), 7.90 (1H, t), 7.36 (1H, t), 7.21 (1H, d), 6.91 (1H, d), 3.03 (4H, m), 1.61 (4H, m), 1.41 (2H, m).

$^{13}$C NMR (400 MHz, CD$_3$OD): 148.8, 147.5, 140.0, 135.6, 133.0, 132.8, 132.0, 129.0, 128.2, 126.3, 124.6, 111.6, 105.4, 48.3, 26.5, 24.6.

LC-MS ESI [M+H]$^+$=358.2

Example 9: Preparation of N-[5-chloro-2-(1H-1,2,3,4-tetrazol-5-yl)phenyl]-3-(piperidine-1-sulfonyl)benzamide 5-chloro-2-(1H-1,2,3,4-tetrazol-5-yl)aniline The commercially available 2-amino-4-chlorobenzonitrile (1 eq., 200 mg, 1.25 mmol), NaN$_3$ (1.37 eq., 111 mg, 0.06 mL, 1.71 mmol) and triethylamine hydrochloride (1.37 eq., 235 mg, 1.71 mmol) were dissolved in toluene (5 mL) and stirred at 80-100° C. overnight.

The solution was allowed to cool to room temperature and water (5 mL) was then added (three times). The aqueous phases were reunified and acidified with concentrated HCl to give a precipitate. The precipitate was filtered off and dried to give the 5-chloro-2-(1H-1,2,3,4-tetrazol-5-yl)aniline as a brown solid (195 mg, 80%).

$^1$H NMR (400 MHz, d6-DMSO): 7.72 (d, 1H, J=8.4 Hz), 6.96 (d, 1H, J=2 Hz), 6.73 (dd, 1H, J=8.4-2 Hz)

$^{13}$C NMR (100 MHz, d6-DMSO): 148.52, 136.24, 129.73, 115.34, 115.09

N-[5-chloro-2-(1H-1,2,3,4-tetrazol-5-yl)phenyl]-3-(piperidine-1-sulfonyl)benzamide To a solution of 3-(piperidine-1-sulfonyl)benzoic acid (1 eq., 100 mg, 0.371 mmol) and BOP (1.2 eq., 197 mg, 0.446 mmol) in DMF (3 mL) was added DIEA (2.5 eq., 119 mg, 0.153 mL, 0.928 mmol). The solution was stirred during 15 minutes before 5-chloro-2-(1H-1,2,3,4-tetrazol-5-yl)aniline (1.1 eq., 79.9 mg, 0.408 mmol) was added. The mixture was stirred overnight at room temperature.

The DMF was evaporated and the mixture diluted in EtOAc and extracted with water and brine. The organic phase was dried over Na$_2$SO$_4$ and filtered. The product was purified using flash chromatography (Silica, EtOAc:MeOH/100:0 to 90:10 over 20 min) affording N-[5-chloro-2-(1H-1,2,3,4-tetrazol-5-yl)phenyl]-3-(piperidine-1-sulfonyl)benzamide as a light brown solid (141 mg, 85%).

$^1$H NMR (400 MHz, d6-DMSO): 12.66 (s, 1H), 8.75 (d, 1H, J=2 Hz), 8.39 (m, 2H), 8.16 (d, 1H, J=8.4 Hz), 7.99 (dt, 1H, J=7.6-1.6 Hz), 7.90 (t, 1H, J=8 Hz), 7.4 (dd, 1H, J=8.4-2.4 Hz), 3.02 (t, 4H, J=1.4 Hz), 1.59 (m, 4H), 1.39 (m, 2H)

$^{13}$C NMR (100 MHz, d6-DMSO): 163.86, 137.48, 136.38, 135.37, 134.24, 131.74, 130.79, 130.26, 129.50, 126.00, 124.01, 120.39, 115.35, 46.71, 24.68, 22.76

LC-MS ESI [M+H]$^+$=447.0

Example 10: Preparation of 5-Chloro-2-hydroxy-N-[3-(piperidine-1sulfonyl)phenyl]benzamide 1-((3-nitrophenyl)sulfonyl)piperidine 3-nitro-benzene sulfonyl chloride (800 mg, 3.61 mmol) was dissolved in DCM (20 mL) and cooled in an ice bath.

Piperidine was added (1.07 ml, 10.83 mmol) and the mixture was stirred at 0° C. for 2 h then at RT overnight. The DCM was evaporated and the mixture diluted in EtOAc and washed with a solution of KHSO4 1N. The organic phase was dried over $Na_2SO_4$ and filtered affording 1-((3-nitrophenyl)sulfonyl)piperidine as a white solid (700 mg, 72%), mp 124° C. (EtOH)

$^1$H NMR (400 MHz, $d_6$-DMSO): 8.54 (dd, 1H, J=1.2 Hz; J=8.2 Hz), 8.36 (dd, 1H, J=1.2 Hz), 8.18 (d, 1H, J=8.2 Hz), 7.95 (t, 1H, J=8.2H).

$^{13}$C NMR (100 MHz, $d_6$-DMSO): 148.07, 137.39, 133.31, 134.47, 127.60, 121.88, 46.50, 24.64, 22.68.

3-(piperidin-1-ylsulfonyl)aniline

Catalytic hydrogenation of 1-((3-nitrophenyl)sulfonyl)piperidine with Pd/C (10%) in ethanol afforded quantitatively the 3-(piperidin-1-ylsulfonyl)aniline as a solid (Mp 114-115 (EtOH—$H_2O$).

$^1$H NMR (400 MHz, $CDCl_3$): 7.27 (t, 1H, J=7.8 Hz), 7.08 (d, 1H, J=7.8 Hz), 6.85 (dd, 1H, J=1.7 Hz), 6.85 (dd, 1H, J=7.8 Hz, J=1.7 Hz), 3.86 (bs, 2H), 2.98 (m, 4H), 1.56 (m, 4H), 1.35 (m, 2H)

$^{13}$C NMR (100 MHz, $CDCl_3$): 147.04, 137.12, 129.80, 118.78, 117.37, 113.41, 47.00, 25.22, 23.55.

5-Chloro-2-hydroxy-N-[3-(piperidine-1sulfonyl) phenyl]benzamide

To a solution of the aniline derivative (60 mg, 1 equiv., 0.25 mmol) in DCM (2.4 mL) 5-chloro-2-hydroxybenzoyl chloride (48 mg; 1 equiv., 0.25 mmol) was added followed by trimethylamine (0.035 mL, 1 equiv., 0.25 mmol) and the reaction was allowed to stir overnight. The organic layer was washed with water, followed by saturated sodium bicarbonate solution, and then dried over $Na_2SO_4$. The solvent was evaporated and the residue was purified by flash chromatography on silica gel (AcOEt-Hex 3/7) affording 5-Chloro-2-hydroxy-N-[3-(piperidine-1sulfonyl) phenyl]benzamide (40 mg (41%)).

$^1$H NMR (400 MHz, d6-DMSO): 8.19 (s, 1H), 8.00 (d, 1H, J=8 Hz), 7.92 (d, 1H, J=2.1 Hz), 7.64 (t, 1H, J=8 Hz), 7.49 (d, 2H, J=8 Hz), 7.03 (d, 1H, J=8 Hz), 3.33 (s, 1H), 2.92 (m, 4H), 1.57 (m, 4H), 1.38 (m, 2H)

$^{13}$C NMR (100 MHz, d6-DMSO): 165.39, 156.58, 138.96, 136.12, 133.11, 129.82, 128.41, 124.57, 122.79, 119.91, 119.02, 46.59, 24.69, 22.81

Example 11: Preparation of N-(5-chloro-2-hydroxyphenyl)-3-[cycloheptyl(methyl)sulfamoyl]benzamide 3-(cycloheptylsulfamoyl)benzoate Cycloheptylamine (1.5 eq., 365 mg, 0.411 mL, 3.2 mmol) and $Et_3N$ (1.5 eq., 323 mg, 0.444 mL, 3.2 mmol) were added to a solution of methyl 3-(chlorosulfonyl)benzoate (1 eq., 500 mg, 2.13 mmol) in $CH_2Cl_2$ (5 mL) at 0° C. The resulting mixture was stirred at room temperature for 1 h. The solvent was evaporated under vacuum. The mixture was diluted in EtOAc and washed with HCl 1N and brine. The organic layer was dried over $Na_2SO_4$ and evaporated under reduce pressure to give methyl 3-(cycloheptylsulfamoyl)benzoate as a brown oil (99%).

$^1$H NMR (400 MHz, $CDCl_3$): 8.50 (td, 1H, J=2-0.4 Hz), 8.21 (ddd, 1H, J=8-2-2 Hz), 8.04 (ddd, 1H, J=8-2-2 Hz), 7.58 (td, 1H, J=8-0.4 Hz), 4.44 (d, 1H, J=8 Hz), 3.94 (s, 3H), 3.38 (m, 1H), 1.50 (m, 12H)

$^{13}$C NMR (100 MHz, $CDCl_3$): 142.07, 133.29, 131.33, 130.96, 129.31, 128.03, 55.03, 52.59, 35.96, 27.89, 23.48 methyl 3-[cycloheptyl(methyl)sulfamoyl]benzoate $CH_3I$ (1.5 eq., 453 mg, 0.199 mL, 3.19 mmol) was added to a solution of methyl 3-(cycloheptylsulfamoyl)benzoate (1 eq., 663 mg, 2.13 mmol) and $K_2CO_3$ (2 eq., 588 mg, 4.26 mmol) in MeCN (5 mL) and the resulting mixture was stirred overnight.

The solvent was then evaporated. EtOAc was added to the crude residue and the organic phase was then washed with HCl 1N and brine. The organic layer was dried over $NA_2SO_4$ and evaporated under reduce pressure to give methyl 3-[cycloheptyl(methyl)sulfamoyl]benzoate (550 mg, 80%).

$^1$H NMR (400 MHz, $CDCl_3$): 8.42 (t, 1H, J=1.6 Hz), 8.20 (dd, 1H, J=8-1.6-1.6 Hz), 7.96 (dt, 1H, J=8-1.6-1.6 Hz), 7.57 (t, 1H, J=8 Hz), 3.94 (m, 4H), 2.73 (s, 3H), 1.45 (m, 12H);

$^{13}$C NMR (100 MHz, $CDCl_3$): 165.84, 141.18, 133.29, 131.48, 131.17, 129.46, 128.21, 58.97, 52.78, 32.69, 28.56, 27.81, 25.21

3-[cycloheptyl(methyl)sulfamoyl]benzoyl chloride

LiOH (5 eq., 354 mg, 8.45 mmol) was added to a solution of methyl 3-[cycloheptyl(methyl)sulfamoyl]benzoate (1 eq., 550 mg, 1.69 mmol) in THF (5 mL) and water (5 mL). The resulting mixture was stirred for 2 h at room temperature. The solution was acidified with HCl 1N the extracted with EtOAc and water. The organic layer was dried over $Na_2SO_4$ and evaporated under vacuum to give methyl 3-[cycloheptyl(methyl)sulfamoyl]benzoate in a quantitative yield. The product was used without further purification and treated with SOCl2 under standard condition to give the corresponding -3-[cycloheptyl(methyl)sulfamoyl]benzoyl chloride.

(5-chloro-2-hydroxyphenyl)-3-[cycloheptyl(methyl) sulfamoyl]benzamide 5-chloro-2-hydroxyaniline (1.1 eq., 274 mg, 1.86 mmol) et $Et_3N$ (1.5 eq., 256 mg, 0.352 mL, 2.53 mmol) were added to a solution of 3-[cycloheptyl(methyl)sulfamoyl]benzoyl chloride (1 eq., 557 mg, 1.69 mmol) in THF (10 mL). The resulting mixture was than stirred at room temperature during 2 h. The solvent was than evaporated and the mixture was extracted with EtOAc and washed with HCl 1N and brine. The organic layer was dried over $Na_2SO_4$ and evaporated under reduce pressure. The solid was then triturated with EtOAc to give N-(5-chloro-2-hydroxyphenyl)-3-[cycloheptyl(methyl)sulfamoyl] benzamide as an off-white solid (170 mg, 23%).

$^1$H NMR (400 MHz, d6-DMSO): 10.08 (s, 1H), 9.87 (s, 1H), 8.33 (t, 1H, J=1.6 Hz), 8.24 (ddd, 1H, J=8-1.6-1.6 Hz), 7.99 (ddd, 1H, J=8-1.6-1.6 Hz), 7.77 (t, 1H, J=8 Hz), 7.72 (d, 1H, J=2.8 Hz), 7.11 (dd, 1H, J=8-2.8 Hz), 6.93 (d, 1H, J=8 Hz), 3.86 (m, 1H), 2.70 (s, 3H), 1.45 (m, 12H)

$^{13}$C NMR (100 MHz, d6-DMSO): 163.91, 148.92, 139.84, 135.19, 131.62, 129.81, 129.54, 126.55, 125.68, 125.59, 124.39, 121.95, 116.98, 58.15, 31.61, 28.55, 27.06, 24.39

LC/MS ESI [M+H]=437.0

Example 12: preparation of 4-chloro-2-(3-(cyclohexylsulfonyl)benzamido)phenyl dihydrogen phosphate dibenzyl (4-chloro-2-(3-(piperidin-1-ylsulfonyl)benzamido)phenyl)phosphate To a solution of N-(5-chloro-2-hydroxyphenyl)-3-(piperidine-1-sulfonyl)benzamide (1 eq., 100 mg, 0.253 mmol) and Et$_3$N (3 eq., 76.9 mg, 0.106 mL, 0.76 mmol) in DCM (1 mL) was added dropwise dibenzyl chlorophosphonate in DCM (1 mL). The resulting solution was than stirred at room temperature for 4 h.

The solution was extracted twice with water and the organic layer was dried over Na$_2$SO$_4$ and evaporated. The product was purified by flash chromatography (Silica gel, Heptane:EtOAc/70:30 to 0:100 over 20 min) to give dibenzyl (4-chloro-2-(3-(piperidin-1-ylsulfonyl)benzamido)phenyl) phosphate.

$^1$H NMR (400 MHz, CDCl$_3$): 9.51 (s, 1H), 8.39 (m, 1H), 8.33 (m, 1H), 8.16 (m, 1H), 7.92 (m, 1H), 7.61 (t, 1H, J=8 Hz), 7.24 (m, 10H), 6.98 (m, 2H), 5.13 (s, 2H), 5.10 (s, 2H), 3.02 (m, 4H), 1.55 (m, 4H), 1.36 (m, 2H)

$^{13}$C NMR (100 MHz, CDCl$_3$): 163.55, 137.57, 135.08, 134.71, 134.65, 131.63, 131.34, 130.87, 130.82, 130.77, 129.58, 129.05, 128.72, 128.25, 126.51, 125.07, 123.49, 122.58, 122.55, 71.22, 71.16, 47.05, 25.16, 23.48

2-(3-(cyclohexylsulfonyl)benzamido)phenyl dihydrogen phosphate

The dibenzyl (4-chloro-2-(3-(piperidin-1-ylsulfonyl)benzamido)phenyl) phosphate was diluted in DCM (3 mL) and TFA (53.2 eq., 1535 mg, 1 mL, 13.5 mmol) was added. The solution was stirred overnight at room temperature. The solvent was evaporated and the product was purified by reverse flash chromatography (H$_2$O:MeCN)

H NMR (400 MHz, d6-DMSO): 10.73 (s, 1H), 8.31 (m, 2H), 8.05 (m, 1H), 8.05 (m, 1H), 7.95 (m, 1H), 7.26 (m, 2H), 2.94 (m, 4H), 1.54 (m, 4H), 1.37 (m, 2H)

$^{13}$C NMR (100 MHz, d6-DMSO): 163.42, (141.87, 141.81), 136.34, (134.96, 134.94), 131.56, (131.21, 131.16), 130.57, 129.91, 128.06, (126.35, 126.29), 125.21, 123.83, (123.40, 123.38), 46.59, 24.64, 22.74

HRMS [M+H]$^+$=475.04841

The following additional compounds were prepared by using the methods described above

N-(5-chloro-2-hydroxy-phenyl)-3-(1-piperidylsulfonyl)benzamide $^1$H NMR (CDCl$_3$): 8.70 (s, H), 8.19 (1H, t, J=1.6 Hz), 8.12 (1H, dt, J=1.6 Hz, 8 Hz), 7.85 (1H, dt, J=1.6 Hz, 8 Hz), 7.62 (t, 1h, 8 Hz), 7.48 (d, 1H, J=2.4 Hz), 7.03 (dd, 1H, J=2.4 Hz, J=8.8 Hz); 8.90 (d, 1H, J=8.8 Hz)

$^{13}$C NMR (CDCl3): 166.5, 146.9, 137.3, 134.4, 132.1, 131.1, 129.9, 126.9, 126.5, 126.1, 125.5, 122.5, 120.0, 47.0, 25.05, 23.3.

LC-MS ESI [M+H]=395.8

N-(5-chloro-2-hydroxy-phenyl)-3-[cyclohexyl(methyl)sulfamoyl]benzamide $^1$H NMR (CDCl$_3$): 8.55 (s, 1H), 8.28 (s, 1H), 8.11 (d, 1H), 7.96 (d, 1H), 7.92 (s, 1H), 7.64 (t, 1H), 7.51 (d, 1H), 7.09 (dd, 1H), 6.95 (d, 1H), 3.75 (tt, 1H), 2.75 (s, 3H), 1.2-1.7 (m, 10H)

$^{13}$C NMR (CDCl$_3$): 165.36, 146.88, 141.45, 134.29, 131.56, 130.39, 130.03, 136.88, 126.48, 125.58, 125.42, 122.25, 120.08, 57.18, 30.39, 28.79, 25.69, 25.21

LC-MS (ESI [M+1]+): 423.1

N-(2-chlorophenyl)-3-(1-piperidylsulfonyl)benzamide

White solid; mp: 150-151° C.

$^1$H NMR (DMSO-d6): 10.52 (s, 1H), 8.29 (d, J=6 Hz, 2H), 7.93 (d, J=9 Hz), 7.84-7.77 (m, 3H), 7.38 (t, J=6 Hz, 2H), 7.13 (t, J=6 Hz, 1H), 2.93 (t, J=6 Hz, 4H), 1.58-1.50 (m, 4H), 1.37-1.32 (m, 2H)

$^{13}$C NMR (DMSO-d6): 164.0, 138.7, 136.0, 135.9, 132.0, 130.1, 129.6, 128.6, 126.4, 124.0, 120.6, 46.6, 24.6, 22.8

HRMS (ESI)[M−H]−: 343.1108

N-(4-chloro-2-hydroxy-phenyl)-3-(1-piperidylsulfonyl)benzamide $^1$H NMR (CDCl$_3$): 8.42 (s, 1H), 8.35 (d, 1H), 8.21 (s, 1H), 8.15 (d, 1H), 7.92 (d, 1H), 7.68 (t, 1H), 7.28 (d, 1H), 7.05 (d, 1H), 6.91 (dd, 1H), 3.00 (t, 4H), 1.62 (m, 4H), 1.43 (m, 2H)

$^{13}$C NMR (CDCl$_3$): 165.44, 159.51, 137.47, 134.24, 132.50, 132.02, 131.14, 129.99, 125.94, 124.25, 123.42, 121.00, 119.76, 47.01, 25.08, 23.37

LC-MS (ESI [M+1]+): 395.0

N-(5-chloro-2-hydroxy-phenyl)-3-(cyclohexylsulfamoyl)-4-methyl-benzamide $^1$H NMR (DMSO-d6): 10.11 (s, 1H), 9.72 (s, 1H), 8.41 (d, 1H), 8.08 (dd, 1H), 7.84 (d, 1H), 7.77 (d, 1H), 7.54 (d, 1H), 7.08 (dd, 1H), 6.93 (d, 1H), 2.95 (m, 1H), 2.65 (s, 3H), 0.90-1.59 (m, 10H)

$^{13}$C NMR (DMSO-d6): 164.07, 148.53, 140.31, 140.29, 132.62, 132.02, 130.94, 127.72, 126.77, 125.30, 123.86, 121.99, 116.90, 51.91, 33.25, 24.82, 24.44, 19.77

LC-MS (ESI [M+1]+): 423.0

4-chloro-2-[2-[3-(1-piperidylsulfonyl)phenyl]-1H-imidazol-5-yl]phenol $^1$H NMR (CDCl$_3$): 8.27 (1H, s), 8.12 (1H, d), 7.75 (1H, d), 7.60 (1H, t), 7.52 (1H, s), 7.44 (1H, s), 6.77-6.70 (2H, m), 2.97 (4H, m), 1.58 (4H, m), 1.38 (2H, m).

$^{13}$C NMR (CD$_3$OD): 153.0, 147.1, 139.8, 131.3, 130.8, 129.5, 128.8, 127.3 (2C), 124.0, 121.9, 119.9, 117.8, 49.0, 24.6, 24.1.

LC-MS ESI [M+H]+=418.0

2-[3-(1-piperidylsulfonyl)phenyl]-3H-benzimidazol-4-ol $^1$H NMR (CD$_3$OD): 8.51 (1H, s), 8.37 (1H, d), 8.04 (1H, d), 7.90 (1H, t), 7.36 (1H, t), 7.21 (1H, d), 6.91 (1H, d), 3.03 (4H, m), 1.61 (4H, m), 1.41 (2H, m).

$^{13}$C NMR (CD$_3$OD): 148.8, 147.5, 140.0, 135.6, 133.0, 132.8, 132.0, 129.0, 128.2, 126.3, 124.6, 111.6, 105.4, 48.3, 26.5, 24.6.

LC-MS ESI [M+H]+=358.2

N-(5-chloro-2-hydroxy-phenyl)-3-(cyclohexylsulfonylamino)benzamide $^1$H NMR (CDCl$_3$): 8.69 (1H, s), 7.70 (1H, s), 7.63 (1H, d), 7.43-7.35 (4H, m), 7.04 (1H, d), 6.91 (1H, m), 3.00 (1H, m), 2.12 (2H, m), 1.82 (2H, m), 1.52 (1H, m), 1.49 (2H, m), 1.23-1.10 (3H, m).

¹³C NMR (CDCl₃): 166.6, 147.1, 137.8, 134.5, 130.3, 126.8, 126.7, 125.3, 124.0, 123.4, 122.5, 120.1, 118.4, 61.1, 26.3, 25.0, 24.9.
LC-MS ESI [M+H]+=408.8

3-[3-aminopropyl(cyclohexyl)sulfamoyl]-N-(5-chloro-2-hydroxy-phenyl)benzamide ¹H NMR (CD₃OD): 8.36 (1H, s), 8.14 (1H, d), 8.03 (1H, d), 7.93 (1H, s), 7.70 (1H, t), 7.00 (1H, d), 6.85 (1H, d), 3.65-3.60 (1H, m), 3.33-3.27 (6H, m), 3.00 (2H, m), 1.99 (2H, m), 1.70 (2H, m), 1.57-1.21 (7H, m), 1.05-1.00 (1H, m).
¹³C NMR (CD₃OD): 149.0, 143.3, 137.0, 132.4, 131.2, 131.2, 128.0, 127.4, 126.7, 125.2, 124.0, 117.6, 60.0, 42.0, 38.4, 32.8, 31.0, 27.2, 26.4.
LC-MS ESI [M+H]+=466.0

N-(3-aminopropyl)-3-(4-chloro-7-hydroxy-1,3-benzoxazol-2-yl)-N-cyclohexyl-benzenesulfonamide ¹H NMR (CD₃OD): 8.64 (1H, s), 8.44 (1H, d), 8.08 (1H, d), 7.80 (1H, t), 7.77 (1H, d), 7.68 (1H, d), 7.42 (1H, d), 3.68 (1H, m), 3.37 (2H, m), 3.07 (2H, m), 2.04 (2H, m), 1.73 (2H, m), 1.60-1.25 (8H, m), 1.07 (1H, m).
¹³C NMR (CD₃OD): 164.3, 151.0, 144.1, 143.8, 132.6, 131.8, 131.2, 129.1, 127.6, 127.0, 121.0, 113.2, 60.1, 42.2, 38.4, 32.9, 31.0, 27.2, 26.3.
LC-MS ESI [M+H]+=448.0

N-(5-chloro-1H-1,3-benzodiazol-2-yl)-3-(piperidine-1-sulfonyl)benzamide

¹H NMR (400 MHz, d6-DMSO): 12.60 (s, 2H), 8.47 (t, 1H, J=1.6 Hz), 8.41 (dt, 1H, J=8-1.6 Hz), 7.94 (dt, 1H, J=8-1.6 Hz), 7.80 (t, 1H, J=8 Hz), 7.49 (d, 1H, J=2 Hz), 7.45 (d, 1H, J=8 Hz), 7.19 (dd, 1H, J=8-2 Hz), 2.94 (t, 4H, J=5.6 Hz), 1.55 (m, 4H), 1.36 (m, 2H)
LC-MS ESI [M+H]⁺=419.0.

N-(5-chloro-2-hydroxyphenyl)-3-[(4-hydroxypiperidin-1-yl)sulfonyl]benzamide

¹H NMR (400 MHz, d6-DMSO): 10.08 (s, 1H), 9.91 (s, 1H), 8.27 (m, 2H), 7.94 (dt, 1H, J=8-1.2 Hz), 7.80 (t, 1H, J=8 Hz), 7.72 (d, 1H, J=2.4 Hz), 7.11 (dd, 1H, J=8-2.4 Hz), 6.93 (d, 1H, J=8 Hz), 3.54 (m, 1H), 3.18 (m, 2H), 2.79 (m, 2H), 1.74 (m, 2H), 1.44 (m, 2H)
¹³C NMR (100 MHz, d6-DMSO): 163.99, 148.99, 136.06, 135.26, 132.03, 130.30, 129.75, 126.51, 126.42, 125.66, 124.51, 121.94, 117.01, 63.67, 43.15, 32.85
LC-MS ESI [M+H]⁺=411.0

N-[5-chloro-2-(N-hydroxycarbamimidoyl)phenyl]-3-(piperidine-1sulfonyl)benzamide ¹H NMR (400 MHz, d6-DMSO): 13.39 (s, 1H), 8.79 (d, 1H, J=2 Hz), 8.53 (s, 1H), 8.22 (m, 2H), 7.98 (m, 3H), 7.88 (t, 1H, J=8 Hz), 7.31 (dd, 1H, J=8-2 Hz), 2.95 (t, 4H, J=5.6 Hz), 1.54 (m, 4H), 1.37 (m, 2H)
¹³C NMR (100 MHz, d6-DMSO): 170.71, 163.89, 141.06, 137.66, 137.04, 135.52, 131.79, 131.33, 131.02, 130.93, 126.10, 123.62, 120.12, 118.39, 47.14, 25.10, 23.21

N-[5-chloro-2-hydroxy-4-(2-methoxyethoxy)phenyl]-3-(piperidine-1-sulfonyl)benzamide ¹H NMR (400 MHz, d6-DMSO): 9.91 (s, 2H), 8.27 (m, 2H), 7.92 (d, 1H, J=8 Hz), 7.79 (t, 1H, J=8 Hz), 7.52 (s, 1H), 6.69 (s, 1H), 4.12 (t, 2H, J=4 Hz), 3.69 (t, 2H, J=4 Hz), 3.35 (s, 3H), 2.93 (m, 4H), 1.55 (m, 4H), 1.37 (m, 2H)
¹³C NMR (100 MHz, d6-DMSO): 164.07, 152.17, 150.81, 135.99, 135.27, 131.99, 130.15, 129.62, 126.87, 126.38, 118.52, 110.25, 102.14, 70.19, 68.32, 58.36, 46.58, 24.64, 22.77
LC-MS ESI [M+H]⁺=369.1188

Ethyl 4-chloro-2-{[3-(piperidine-1-sulfonyl)phenyl]amido}benzoate

¹H NMR (400 MHz, CDCl₃): 8.98 (d, 1H, J=2 Hz), 8.38 (t, 1H, J=1.6 Hz), 8.21 (ddd, 1H, J=8-1.6-1.6 Hz), 8.02 (d, 1H, J=8 Hz), 7.95 (ddd, 1H, J=8-1.6-1.6 Hz), 7.69 (t, 1H, J=8 Hz), 7.11 (dd, 1H, J=8-2 Hz), 4.4 (q, 2H, J=7.2 Hz), 3.05 (t, 4H, J=6 Hz), 1.65 (m, 4H), 1.41 (t, 3H, J=7.2 Hz), 1.40 (m, 2H)
¹³C NMR (100 MHz, CDCl₃): 168.38, 164.27, 142.52, 141.42, 137.86, 135.91, 132.27, 131.36, 131.14, 129.92, 126.76, 123.56, 120.56, 113.96, 62.17, 47.28, 25.42, 23.71, 14.38;
LC-MS ESI [M+H]⁺=451.0

N-(5-chloro-2-hydroxyphenyl)-3-{[4-(pyrimidin-2-yl)piperazin-1-yl]sulfonyl}benzamide ¹H NMR (400 MHz, d6-DMSO): 10.07 (s, 1H), 9.89 (s, 1H), 8.33 (m, 2H), 8.26 (m, 2H), 7.95 (m, 1H), 7.79 (t, 1H, J=8 Hz), 7.72 (d, 1H, J=2.4 Hz), 7.10 (dd, 1H, J=8-2.4 Hz), 6.93 (d, 1H, J=8 Hz), 6.63 (t, 1H, J=4.8 Hz), 3.84 (t, 4H, J=4.8 Hz), 3.01 (t, 4H, J=4.8 Hz)
¹³C NMR (100 MHz, d6-DMSO): 164.04, 160.75, 157.98, 148.34, 135.46, 135.30, 132.33, 130.42, 129.86, 126.55, 126.52, 125.34, 124.44, 121.95, 117.00, 110.68, 45.65, 42.53
LC-MS ESI [M+H]⁺=474.0

Example 13: Pharmacological Activities of Compounds of the Invention

The pharmacological activities of the compounds of the invention were assessed as described previously and are illustrated in the table hereunder

|         | IC50, μM | |
| ------- | ------- | ---------------- |
| Example | Binding | Autophosphorylation |
| 1  | 11.8 | 58 |
| 4  | 26   | 20 |
| 5  | 33   | 17 |
| 7  | 10   | 63 |
| 8  | 98   | 68 |
| 9  | 175  | 148 |
| 10 | 4.6  | 116 |
| 11 | 27.5 | 41 |

REFERENCES

Throughout this application, various references describe the state of the art to which this invention pertains. The disclosures of these references are hereby incorporated by reference into the present disclosure.

Caterina, M. J., Leffler, A., Malmberg, A. B., Martin, W. J., Trafton, J., Petersen-Zeitz, K. R., Koltzenburg, M., Basbaum, A. I., and Julius, D.; Impaired nociception and pain sensation in mice lacking the capsaicin receptor; Science 2000 288, 306-313.

Chuang, H. H., Prescott, E. D., Kong, H., Shields, S., Jordt, S. E., Basbaum, A. I., Chao, M. V., and Julius, D.; Bradykinin and nerve growth factor release the capsaicin receptor from PtdIns(4,5)P2-mediated inhibition; Nature 2001 411, 957-962.

Davis, J. B., Gray, J., Gunthorpe, M. J., Hatcher, J. P., Davey, P. T., Overend, P., Harries, M. H., Latcham, J., Clapham, C., Atkinson, K.; Vanilloid receptor-1 is essential for inflammatory thermal hyperalgesia; Nature 2000 405, 183-187.

Jordt, S. E., McKemy, D. D., and Julius, D.; Lessons from peppers and peppermint: the molecular logic of thermosensation; Curr Opin Neurobiol 200313, 487-492.

Malin, S. A., Molliver, D. C., Koerber, H. R., Cornuet, P., Frye, R., Albers, K. M., and Davis, B. M.; Glial cell line-derived neurotrophic factor family members sensitize nociceptors in vitro and produce thermal hyperalgesia in vivo; J Neurosci 2006 26, 8588-8599.

Zarrinkar P P, Gunawardane R N, Cramer M D, Gardner M F, Brigham D, Belli B, Karaman M W, Pratz K W, Pallares G, Chao Q, Sprankle K G, Patel H K, Levis M, Armstrong R C, James J, Bhagwat S S; AC220 is a uniquely potent and selective inhibitor of FLT3 for the treatment of acute myeloid leukemia (AML); Blood. 2009 Oct. 1; 114(14): 2984-92.

The invention claimed is:

1. A method of treating chronic pain or neuropathic pain in a patient in need thereof comprising
administering to the patient a therapeutically effective amount of a compound of general formula (2)

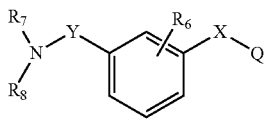
(2)

wherein
X is selected from a bond, CO, NH, CONH, NHCO and a 5- or 6-member heteroaromatic group comprising 2 or 3 N atoms;
Y represents $SO_2$,
Q is selected from a group of formula:

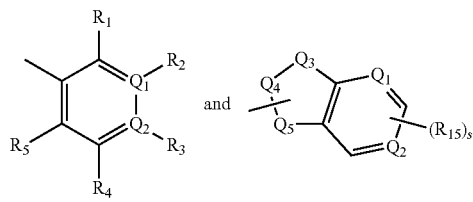

$R_1$ is selected from halo, $OR_{11}$, COO $R_{11}$, 1H-tetrazolyl; $PO_4H_2$, amidino and N-hydroxyamidino;
$R_2$ is selected from H, alkyl, halo, $OR_{11}$ and $COR_{11}$;
$R_3$ is selected from H, $OR_{11}$, halo and O—$(CH_2)_p$—O-alkyl;
$R_4$ is selected from H, alkyl, halo, CN, trifluoromethyl, CO-alkyl, phenyl and benzyl;
$R_5$ is H;
or $R_1$ is as defined above and two from $R_2$ and $R_3$ or $R_3$ and $R_4$ or $R_4$ and $R_5$ together with the carbon atoms to which they are attached form an aromatic ring comprising 5 to 6 members, and the others from $R_2$ to $R_5$ represent H;
$R_6$ is selected from H, OH, halo, alkyl, hydroxyalkyl and alkoxy,
or $R_1$ together with $R_6$ form a O or a NH chain;
$R_7$ is selected from H, alkyl, cycloalkyl, phenyl, benzyl, $(CH_2)_q$-$R_{12}$,
$R_8$ is selected from H, alkyl, cycloalkyl, adamantyl, pyridyl, $(CH_2)_r$—$R_{13}$,
or $R_7$ and $R_8$ together with the N atom to which they are attached form a group of formula:

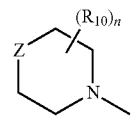

wherein Z is a bond or Z is selected from $CHR_{14}$, $CH_2CHR_{14}$, $NR_{14}$, $CH_2NR_{14}$, and O,
$R_{10}$ is selected from H, alkyl, halo, trifluoromethyl, aryl and hydroxyalkyl,
or two adjacent $R_{10}$ groups together with the cyclic atoms to which they are attached form an aryl group; and
$R_{11}$ is H or alkyl;
$R_{12}$ is selected from OH, COOH, CO-alkyl, phenyl, morpholino, $NH_2$, NH-alkyl, N-(alkyl)$_2$ NH(NH) $NH_2$, $CH_2COO$-alkyl,
$R_{13}$ is selected from OH, and phenyl;
$R_{14}$ is selected from H, alkyl, cycloalkyl, aryl, and arylalkyl, wherein the cycloalkyl or aryl ring may comprise one or two heteroatoms in the cyclic structure selected from N and O and may be substituted with one or more substituent selected from alkyl,
halo, cyano, amino, alkyl amino, dialkyamino, nitro, trifluoromethyl, aryl, alkyl-aryl, acyl, alkyloxy or aryloxy,
$R_{15}$ represents a group selected from H, halo, OH and alkoxy;
one of $Q_1$ and $Q_2$ is CH and the other N;
$Q_3$ is selected from O, S, N and NH;
$Q_4$ is selected from C and N, and CO;
$Q_5$ is selected from C and N;
n is 0, 1 or 2;
p is 1, 2, 3 or 4;
q is 0, 1, 2, 3 or 4;
r is 0, 1, 2, 3 or 4;
s is 0, 1, 2 or 3;
or a pharmaceutically acceptable salt thereof.

2. The method of claim 1, wherein the compound is selected from the group consisting of:
N-(5-chloro-2-hydroxy-phenyl)-3-(1-piperidylsulfonyl) benzamide;
N-(5-fluoro-2-hydroxy-phenyl)-3-(1-piperidylsulfonyl) benzamide;
N-(5-bromo-2-hydroxy-phenyl)-3-(1-piperidylsulfonyl) benzamide;
N-(2-hydroxy-5-phenyl-phenyl)-3-(1-piperidylsulfonyl) benzamide;
N-(5-benzyl-2-hydroxy-phenyl)-3-(1-piperidylsulfonyl) benzamide;
N-[2-hydroxy-5-(trifluoromethyl)phenyl]-3-(1-piperidylsulfonyl)benzamide;

N-(5-cyano-2-hydroxy-phenyl)-3-(1-piperidylsulfonyl)benzamide;
N-(5-acetyl-2-hydroxy-phenyl)-3-(1-piperidylsulfonyl)benzamide;
N-[5-(1,1-dimethylpropyl)-2-hydroxy-phenyl]-3-(1-piperidylsulfonyl)benzamide;
N-(2-hydroxy-4-methoxy-phenyl)-3-(1-piperidylsulfonyl)benzamide;
N-(3-hydroxy-2-naphthyl)-3-(1-piperidylsulfonyl)benzamide;
N-(2-hydroxy-1-naphthyl)-3-(1-piperidylsulfonyl)benzamide;
5-chloro-2-hydroxy-N-[3-(1-piperidylsulfonyl)phenyl]benzamide;
N-(5-chloro-2-hydroxy-phenyl)-4-methyl-3-(1-piperidylsulfonyl)benzamide;
N-(5-chloro-2-hydroxy-phenyl)-3-(dimethylsulfamoyl)benzamide;
N-(5-chloro-2-hydroxy-phenyl)-3-(cyclohexylsulfamoyl)benzamide;
3-(azepan-1-ylsulfonyl)-N-(5-chloro-2-hydroxy-phenyl)benzamide;
N-(5-chloro-2-hydroxy-phenyl)-3-[(2-methyl-1-piperidyl)sulfonyl]benzamide;
N-(5-chloro-2-hydroxy-phenyl)-3-[(3-methyl-1-piperidyl)sulfonyl]benzamide;
N-(5-chloro-2-hydroxy-phenyl)-3-[(4-methyl-1-piperidyl)sulfonyl]benzamide;
3-[(4-benzyl-1-piperidyl)sulfonyl]-N-(5-chloro-2-hydroxy-phenyl)benzamide;
N-(5-chloro-2-hydroxy-phenyl)-3-[[4-(1-piperidyl)-1-piperidyl]sulfonyl]benzamide;
N-(5-chloro-2-hydroxy-phenyl)-3-(4-methylpiperazin-1-yl)sulfonyl-benzamide;
N-(5-chloro-2-hydroxy-phenyl)-3-(4-phenylpiperazin-1-yl)sulfonyl-benzamide;
3-(4-benzylpiperazin-1-yl)sulfonyl-N-(5-chloro-2-hydroxy-phenyl)benzamide;
N-(5-chloro-1H-indol-7-yl)-3-(1-piperidylsulfonyl)benzamide;
5-chloro-3-[3-(1-piperidylsulfonyl)benzoyl]-1H-benzimidazol-2-one;
3-(1-adamantylsulfamoyl)-N-(5-chloro-2-hydroxy-phenyl)benzamide;
N-(5-chloro-2-hydroxy-phenyl)-3-[cyclohexyl(methyl)sulfamoyl]benzamide;
N-(5-chloro-2-hydroxy-phenyl)-3-[[2-(hydroxymethyl)-1-piperidyl]sulfonyl]benzamide;
N-(5-chloro-2-hydroxy-phenyl)-3-(4-pyrimidin-2-ylpiperazin-1-yl)sulfonyl-benzamide;
N-(5-chloro-2-hydroxy-phenyl)-3-[(3-phenyl-1-piperidyl)sulfonyl]benzamide;
N-(5-chloro-2-hydroxy-phenyl)-3-[[3-(hydroxymethyl)-1-piperidyl]sulfonyl]benzamide;
N-(5-chloro-2-hydroxy-phenyl)-3-pyrrolidin-1-ylsulfonyl-benzamide;
N-(5-chloro-2-hydroxy-phenyl)-3-morpholinosulfonyl-benzamide;
N-(5-chloro-2-hydroxy-phenyl)-3-indolin-1-ylsulfonyl-benzamide;
N-(2-chlorophenyl)-3-(1-piperidylsulfonyl)benzamide;
N-(2,5-dichlorophenyl)-3-(1-piperidylsulfonyl)benzamide;
N-(5-chloro-2-fluoro-phenyl)-3-(1-piperidylsulfonyl)benzamide;
N-(4-chloro-2-hydroxy-phenyl)-3-(1-piperidylsulfonyl)benzamide;
2-chloro-N-(5-chloro-2-hydroxy-phenyl)-5-(1-piperidylsulfonyl)benzamide;
N-(5-chloro-2-hydroxy-phenyl)-2-fluoro-5-(1-piperidylsulfonyl)benzamide;
N-(5-chloro-2-hydroxy-phenyl)-3-(cyclohexylsulfamoyl)-4-methyl-benzamide;
N-(5-chloro-2-hydroxy-phenyl)-3-(2-pyridylsulfamoyl)benzamide;
N-(5-chloro-2-hydroxy-phenyl)-2-methyl-5-(1-piperidylsulfonyl)benzamide;
N-(4-hydroxy-3-pyridyl)-3-(1-piperidylsulfonyl)benzamide;
2-hydroxy-N-(2-hydroxyphenyl)-5-(1-piperidylsulfonyl)benzamide;
N-(5-chloro-2-hydroxy-phenyl)-3-(2-phenylethylsulfamoyl)benzamide;
N-(5-chloro-2-hydroxy-phenyl)-3-(4-phenylbutylsulfamoyl)benzamide;
N-(5-chloro-2-hydroxy-phenyl)-3-(2-hydroxyethylsulfamoyl)benzamide;
N-[3-(1-piperidylsulfonyl)phenyl]-1H-indazol-3-amine;
4-chloro-2-[2-[3-(1-piperidylsulfonyl)phenyl]-1H-imidazol-5-yl]phenol;
3-[benzyl(cyclohexyl)sulfamoyl]-N-(5-chloro-2-hydroxy-phenyl)benzamide;
tert-butyl 2-[[3-[(5-chloro-2-hydroxy-phenyl)carbamoyl]phenyl]sulfonyl-cyclohexyl-amino]acetate;
N-(5-chloro-2-hydroxy-phenyl)-3-[cyclohexyl(3-phenylpropyl)sulfamoyl]benzamide;
N-(5-chloro-2-hydroxy-phenyl)-3-(4-hydroxybutylsulfamoyl)benzamide;
2-[[3-[(5-chloro-2-hydroxy-phenyl)carbamoyl]phenyl]sulfonyl-cyclohexyl-amino]acetic acid;
2-[3-(1-piperidylsulfonyl)phenyl]-3H-benzimidazol-4-ol;
3-[3-aminopropyl(cyclohexyl)sulfamoyl]-N-(5-chloro-2-hydroxy-phenyl)benzamide;
N-(3-aminopropyl)-3-(5-chloro-1,3-benzoxazol-2-yl)-N-cyclohexyl-benzenesulfonamide;
N-(5-chloro-2-hydroxy-phenyl)-3-[cyclohexyl(3-guanidinopropyl)sulfamoyl]benzamide;
N-(4,5-dichloro-2-hydroxy-phenyl)-3-(1-piperidylsulfonyl)benzamide;
5-chloro-N-[3-(1-piperidylsulfonyl)phenyl]-1H-indazol-3-amine;
N-(3-chloro-2-hydroxy-phenyl)-3-(1-piperidylsulfonyl)benzamide;
3-chloro-8-(1-piperidylsulfonyl)-5H-benzo[b][1,4]benzoxazepin-6-one;
3-chloro-8-(1-piperidylsulfonyl)-5,11-dihydrobenzo[b][1,4]benzodiazepin-6-one;
5-chloro-2-[3-(1-piperidylsulfonyl)phenyl]-1,3-benzoxazole;
4-chloro-2-[3-[3-(1-piperidylsulfonyl)phenyl]-1H-1,2,4-triazol-5-yl]phenol;
7-chloro-2-[3-(1-piperidylsulfonyl)phenyl]-3H-benzimidazol-4-ol;
5,7-dichloro-2-[3-(1-piperidylsulfonyl)phenyl]-3H-benzimidazol-4-ol;
4-[[3-[(5-chloro-2-hydroxy-phenyl)carbamoyl]phenyl]sulfonyl-cyclohexyl-amino]butanoic acid;
N-(5-chloro-2-hydroxy-phenyl)-3-[cyclohexyl(5-phenylpentyl)sulfamoyl]benzamide;
N-(5-chloro-2-hydroxy-phenyl)-3-[cyclohexyl(3-hydroxypropyl)sulfamoyl]benzamide;
N-(5-chloro-2-hydroxy-phenyl)-3-methyl-5-(1-piperidylsulfonyl)benzamide;

N-(5-chloro-2-hydroxy-phenyl)-3-[cyclopentyl(methyl) sulfamoyl]benzamide;
3-[2-aminoethyl(cyclohexyl)sulfamoyl]-N-(5-chloro-2-hydroxy-phenyl)benzamide;
N-(2-aminoethyl)-3-(5-chloro-1,3-benzoxazol-2-yl)-N-cyclohexyl-benzenesulfonamide;
3-[4-aminobutyl(cyclohexyl)sulfamoyl]-N-(5-chloro-2-hydroxy-phenyl)benzamide;
N-(4-aminobutyl)-3-(5-chloro-1,3-benzoxazol-2-yl)-N-cyclohexyl-benzenesulfonamide;
N-(5-chloro-2-hydroxy-phenyl)-3-[cycloheptyl(methyl) sulfamoyl]benzamide;
N-(3-aminopropyl)-3-[5-(5-chloro-2-hydroxy-phenyl)-1H-1,2,4-triazol-3-yl]-N-cyclohexyl-benzenesulfonamide;
N-(5-chloro-2-hydroxy-phenyl)-3-[cyclohexyl-[3-(dimethylamino)propyl]sulfamoyl]benzamide;
3-(5-chloro-1,3-benzoxazol-2-yl)-N-cyclohexyl-N-[3-(dimethylamino)propyl]benzenesulfonamide;
4-chloro-2-[4-[3-(1-piperidylsulfonyl)phenyl]triazol-1-yl]phenol;
4-chloro-2-[4-[3-(1-piperidylsulfonyl)phenyl]pyrimidin-2-yl]phenol;
N-(3-aminopropyl)-3-(1,3-benzothiazol-2-yl)-N-cyclohexyl-benzenesulfonamide;
3-[3-aminopropyl(cyclohexyl)sulfamoyl]-N-(2-methoxy-phenyl)benzamide;
3-(1,3-benzoxazol-2-yl)-N-cyclohexyl-N-methyl-benzenesulfonamide;
3-[3-aminopropyl(cyclohexyl)sulfamoyl]-N-(2-hydroxy-phenyl)benzamide;
N-(3-aminopropyl)-3-(1,3-benzoxazol-2-yl)-N-cyclohexyl-benzenesulfonamide;
3-[3-aminopropyl(cyclohexyl)sulfamoyl]-N-(2-hydroxy-3-methoxy-phenyl)benzamide;
N-(3-aminopropyl)-N-cyclohexyl-3-(7-methoxy-1,3-benzoxazol-2-yl)benzenesulfonamide;
N-(3-aminopropyl)-N-cyclohexyl-3-thiazolo[5,4-b]pyridin-2-yl-benzenesulfonamide;
2-[3-(1-piperidylsulfonyl)phenyl]benzotriazole;
N-(3-aminopropyl)-N-cyclohexyl-3-thiazolo[4,5-c]pyridin-2-yl-benzenesulfonamide;
N-(3-aminopropyl)-N-cyclohexyl-3-(7-hydroxy-1,3-benzoxazol-2-yl)benzenesulfonamide;
3-[3-aminopropyl(cyclohexyl)sulfamoyl]-N-(4,5-dichloro-2-hydroxy-phenyl)benzamide;
N-(3-aminopropyl)-N-cyclohexyl-3-(5,6-dichloro-1,3-benzoxazol-2-yl)benzenesulfonamide;
N-(3-aminopropyl)-3-(1H-benzimidazol-2-yl)-N-cyclohexyl-benzenesulfonamide;
N-(5-chloro-2-hydroxy-phenyl)-3-[cyclohexyl(3-morpholinopropyl)sulfamoyl]benzamide;
3-(5-chloro-1,3-benzoxazol-2-yl)-N-cyclohexyl-N-(3-morpholinopropyl)benzenesulfonamide;
3-(5-chloro-1,3-benzoxazol-2-yl)-N-cyclohexyl-N-(3-hydroxypropyl)benzenesulfonamide;
3-[5-(5-chloro-2-hydroxy-phenyl)-1H-1,2,4-triazol-3-yl]-N-cyclohexyl-N-methyl-benzenesulfonamide;
N-[5-chloro-2-hydroxy-4-(2-methoxyethoxy)phenyl]-3-(1-piperidylsulfonyl)benzamide;
N-(5-chloro-2-hydroxy-phenyl)-3-[cycloheptyl(methyl) sulfamoyl]benzamide;
ethyl 4-chloro-2-[[3-(1-piperidylsulfonyl)benzoyl]amino] benzoate;
N-(5-chloro-2-hydroxy-phenyl)-3-[(4-hydroxy-1-piperidyl)sulfonyl]benzamide;
4-chloro-2-[[3-(1-piperidylsulfonyl)benzoyl]amino]benzoic acid;
N-(3,5-dichloro-2-hydroxy-phenyl)-3-(1-piperidylsulfonyl)benzamide;
N-(5-chloro-1H-benzimidazol-2-yl)-3-(1-piperidylsulfonyl)benzamide;
N-(5-chloro-2-hydroxy-phenyl)-3-[(4,4-difluoro-1-piperidyl)sulfonyl]benzamide;
N-(3-acetyl-5-chloro-2-hydroxy-phenyl)-3-(1-piperidylsulfonyl)benzamide;
N-(5-chloro-2-hydroxy-3-methyl-phenyl)-3-(1-piperidylsulfonyl)benzamide;
N-[5-chloro-2-(1H-tetrazol-5-yl)phenyl]-3-(1-piperidylsulfonyl)benzamide;
N-[5-chloro-2-(N-hydroxycarbamimidoyl)phenyl]-3-(1-piperidylsulfonyl)benzamide;
N-(5-chloro-3-fluoro-2-hydroxy-phenyl)-3-(1-piperidylsulfonyl)benzamide; and
[4-chloro-2-[[3-(1-piperidylsulfonyl)benzoyl]amino]phenyl] dihydrogen phosphate.

3. A compound of general formula (2)

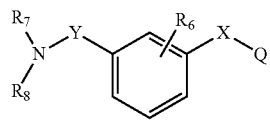

wherein:
X is CO—NH or triazolyl,
Y represents SO$_2$,
Q is selected from a group of formula:

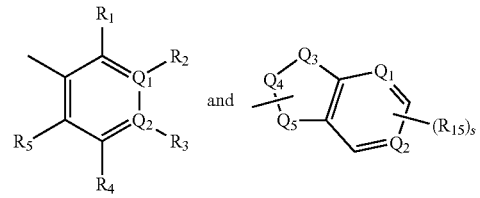

$Q_1$ and $Q_2$ are CH,
$Q_3$ is selected from O, S, N and NH,
$Q_4$ is selected from C and N, and CO,
$Q_5$ is selected from C and N,
$R_6$ is selected from H, OH, alkyl, hydroxyalkyl and alkoxy,
$R_1$ represents OH,
$R_2$ represents H,
$R_3$ is selected from H, OR$_{11}$, halo and O—(CH$_2$)$_p$—O-alkyl;
$R_4$ is selected from H, alkyl, halo, CN, trifluoromethyl, CO-alkyl, phenyl and benzyl;
with the proviso that one from $R_3$ and $R_4$ is H;
$R_5$ is H,
two from $R_2$ and $R_3$ or $R_3$ and $R_4$ or $R_4$ and $R_5$ together with the carbon atoms to which they are attached form an aromatic ring comprising 5 to 6 members, and the others from $R_2$ to $R_5$ represent H, $R_7$ and $R_8$ represent alkyl, or $R_7$ and $R_8$ together with the N atom to which they are attached form a group of formulae:

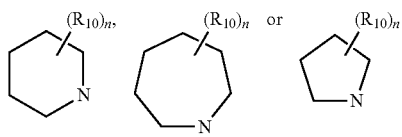

wherein $R_{10}$ is selected from H, alkyl, halo, trifluoromethyl, aryl and hydroxyalkyl or two adjacent $R_{10}$ groups together with the cyclic atoms to which they are attached form an aryl group; or $R_7$ and $R_8$ together with the N atom to which they are attached form a group of formula:

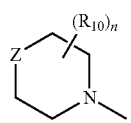

wherein Z is a $NR_{14}$ group, wherein $R_{14}$ is selected from phenyl, benzyl and pyrimidyl, or $R_7$ is H and $R_8$ is cycloalkyl, preferably cyclohexyl and adamantyl, $R_{11}$ is H or alkyl, $R_{15}$ represents a group selected from H, halo, OH and alkoxy, s is 0, 1, 2 or 3, n is 1.

4. A compound of general formula (2a)

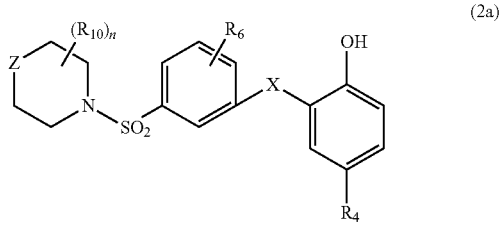

wherein X, Z and $R_{10}$ and n are as defined in claim 1, R6 is as defined in claim 3 and $R_4$ is selected from alkyl, halo, CN, trifluoromethyl, CO-alkyl, phenyl and benzyl, with the exclusion of N-(5-chloro-2-hydroxyphenyl)-3-(piperidine-1-sulfonyl)benzamide.

5. A compound selected from the group consisting of:
N-(5-fluoro-2-hydroxy-phenyl)-3-(1-piperidylsulfonyl)benzamide;
N-(5-bromo-2-hydroxy-phenyl)-3-(1-piperidylsulfonyl)benzamide;
N-(2-hydroxy-5-phenyl-phenyl)-3-(1-piperidylsulfonyl)benzamide;
N-(5-benzyl-2-hydroxy-phenyl)-3-(1-piperidylsulfonyl)benzamide;
N-[2-hydroxy-5-(trifluoromethyl)phenyl]-3-(1-piperidylsulfonyl)benzamide;
N-(5-cyano-2-hydroxy-phenyl)-3-(1-piperidylsulfonyl)benzamide;
N-(5-acetyl-2-hydroxy-phenyl)-3-(1-piperidylsulfonyl)benzamide;
N-[5-(1,1-dimethylpropyl)-2-hydroxy-phenyl]-3-(1-piperidylsulfonyl)benzamide;
N-(2-hydroxy-4-methoxy-phenyl)-3-(1-piperidylsulfonyl)benzamide;
N-(3-hydroxy-2-naphthyl)-3-(1-piperidylsulfonyl)benzamide;
N-(2-hydroxy-1-naphthyl)-3-(1-piperidylsulfonyl)benzamide;
5-chloro-2-hydroxy-N-[3-(1-piperidylsulfonyl)phenyl]benzamide;
N-(5-chloro-2-hydroxy-phenyl)-4-methyl-3-(1-piperidylsulfonyl)benzamide;
N-(5-chloro-2-hydroxy-phenyl)-3-(dimethylsulfamoyl)benzamide;
N-(5-chloro-2-hydroxy-phenyl)-3-(cyclohexylsulfamoyl)benzamide;
3-(azepan-1-ylsulfonyl)-N-(5-chloro-2-hydroxy-phenyl)benzamide;
N-(5-chloro-2-hydroxy-phenyl)-3-[(2-methyl-1-piperidyl)sulfonyl]benzamide;
N-(5-chloro-2-hydroxy-phenyl)-3-[(3-methyl-1-piperidyl)sulfonyl]benzamide;
N-(5-chloro-2-hydroxy-phenyl)-3-[(4-methyl-1-piperidyl)sulfonyl]benzamide;
3-[(4-benzyl-1-piperidyl)sulfonyl]-N-(5-chloro-2-hydroxy-phenyl)benzamide;
N-(5-chloro-2-hydroxy-phenyl)-3-[[4-(1-piperidyl)-1-piperidyl]sulfonyl]benzamide;
N-(5-chloro-2-hydroxy-phenyl)-3-(4-methylpiperazin-1-yl)sulfonyl-benzamide;
N-(5-chloro-2-hydroxy-phenyl)-3-(4-phenylpiperazin-1-yl)sulfonyl-benzamide;
3-(4-benzylpiperazin-1-yl)sulfonyl-N-(5-chloro-2-hydroxy-phenyl)benzamide;
N-(5-chloro-1H-indol-7-yl)-3-(1-piperidylsulfonyl)benzamide;
5-chloro-3-[3-(1-piperidylsulfonyl)benzoyl]-1H-benzimidazol-2-one;
3-(1-adamantylsulfamoyl)-N-(5-chloro-2-hydroxy-phenyl)benzamide;
N-(5-chloro-2-hydroxy-phenyl)-3-[cyclohexyl(methyl)sulfamoyl]benzamide;
N-(5-chloro-2-hydroxy-phenyl)-3-[[2-(hydroxymethyl)-1-piperidyl]sulfonyl]benzamide;
N-(5-chloro-2-hydroxy-phenyl)-3-(4-pyrimidin-2-ylpiperazin-1-yl)sulfonyl-benzamide;
N-(5-chloro-2-hydroxy-phenyl)-3-[(3-phenyl-1-piperidyl)sulfonyl]benzamide;
N-(5-chloro-2-hydroxy-phenyl)-3-[[3-(hydroxymethyl)-1-piperidyl]sulfonyl]benzamide;
N-(5-chloro-2-hydroxy-phenyl)-3-pyrrolidin-1-ylsulfonyl-benzamide;
N-(5-chloro-2-hydroxy-phenyl)-3-morpholinosulfonyl-benzamide;
N-(5-chloro-2-hydroxy-phenyl)-3-indolin-1-ylsulfonyl-benzamide;
N-(2,5-dichlorophenyl)-3-(1-piperidylsulfonyl)benzamide;
N-(5-chloro-2-fluoro-phenyl)-3-(1-piperidylsulfonyl)benzamide;
N-(4-chloro-2-hydroxy-phenyl)-3-(1-piperidylsulfonyl)benzamide;
N-(5-chloro-2-hydroxy-phenyl)-2-fluoro-5-(1-piperidylsulfonyl)benzamide;
N-(5-chloro-2-hydroxy-phenyl)-3-(cyclohexylsulfamoyl)-4-methyl-benzamide;

N-(5-chloro-2-hydroxy-phenyl)-3-(2-pyridylsulfamoyl)benzamide;
N-(5-chloro-2-hydroxy-phenyl)-2-methyl-5-(1-piperidylsulfonyl)benzamide;
N-(4-hydroxy-3-pyridyl)-3-(1-piperidylsulfonyl)benzamide;
2-hydroxy-N-(2-hydroxyphenyl)-5-(1-piperidylsulfonyl)benzamide;
N-(5-chloro-2-hydroxy-phenyl)-3-(2-phenylethylsulfamoyl)benzamide;
N-(5-chloro-2-hydroxy-phenyl)-3-(4-phenylbutylsulfamoyl)benzamide;
N-(5-chloro-2-hydroxy-phenyl)-3-(2-hydroxyethylsulfamoyl)benzamide;
N-[3-(1-piperidylsulfonyl)phenyl]-1H-indazol-3-amine;
4-chloro-2-[2-[3-(1-piperidylsulfonyl)phenyl]-1H-imidazol-5-yl]phenol;
3-[benzyl(cyclohexyl)sulfamoyl]-N-(5-chloro-2-hydroxy-phenyl)benzamide;
tert-butyl 2-[[3-[(5-chloro-2-hydroxy-phenyl)carbamoyl]phenyl]sulfonyl-cyclohexyl-amino]acetate;
N-(5-chloro-2-hydroxy-phenyl)-3-[cyclohexyl(3-phenylpropyl)sulfamoyl]benzamide;
N-(5-chloro-2-hydroxy-phenyl)-3-(4-hydroxybutylsulfamoyl)benzamide;
2-[[3-[(5-chloro-2-hydroxy-phenyl)carbamoyl]phenyl]sulfonyl-cyclohexyl-amino]acetic acid;
2-[3-(1-piperidylsulfonyl)phenyl]-3H-benzimidazol-4-ol;
3-[3-aminopropyl(cyclohexyl)sulfamoyl]-N-(5-chloro-2-hydroxy-phenyl)benzamide;
N-(3-aminopropyl)-3-(5-chloro-1,3-benzoxazol-2-yl)-N-cyclohexyl-benzenesulfonamide;
N-(5-chloro-2-hydroxy-phenyl)-3-[cyclohexyl(3-guanidinopropyl)sulfamoyl]benzamide;
N-(4,5-dichloro-2-hydroxy-phenyl)-3-(1-piperidylsulfonyl)benzamide;
5-chloro-N-[3-(1-piperidylsulfonyl)phenyl]-1H-indazol-3-amine;
N-(3-chloro-2-hydroxy-phenyl)-3-(1-piperidylsulfonyl)benzamide;
3-chloro-8-(1-piperidylsulfonyl)-5H-benzo[b][1,4]benzoxazepin-6-one;
3-chloro-8-(1-piperidylsulfonyl)-5,11-dihydrobenzo[b][1,4]benzodiazepin-6-one;
5-chloro-2-[3-(1-piperidylsulfonyl)phenyl]-1,3-benzoxazole;
4-chloro-2-[3-[3-(1-piperidylsulfonyl)phenyl]-1H-1,2,4-triazol-5-yl]phenol;
7-chloro-2-[3-(1-piperidylsulfonyl)phenyl]-3H-benzimidazol-4-ol;
5,7-dichloro-2-[3-(1-piperidylsulfonyl)phenyl]-3H-benzimidazol-4-ol;
4-[[3-[(5-chloro-2-hydroxy-phenyl)carbamoyl]phenyl]sulfonyl-cyclohexyl-amino]butanoic acid;
N-(5-chloro-2-hydroxy-phenyl)-3-[cyclohexyl(5-phenylpentyl)sulfamoyl]benzamide;
N-(5-chloro-2-hydroxy-phenyl)-3-[cyclohexyl(3-hydroxypropyl)sulfamoyl]benzamide;
N-(5-chloro-2-hydroxy-phenyl)-3-methyl-5-(1-piperidylsulfonyl)benzamide;
N-(5-chloro-2-hydroxy-phenyl)-3-[cyclopentyl(methyl)sulfamoyl]benzamide;
3-[2-aminoethyl(cyclohexyl)sulfamoyl]-N-(5-chloro-2-hydroxy-phenyl)benzamide;
N-(2-aminoethyl)-3-(5-chloro-1,3-benzoxazol-2-yl)-N-cyclohexyl-benzenesulfonamide;
3-[4-aminobutyl(cyclohexyl)sulfamoyl]-N-(5-chloro-2-hydroxy-phenyl)benzamide;
N-(4-aminobutyl)-3-(5-chloro-1,3-benzoxazol-2-yl)-N-cyclohexyl-benzenesulfonamide;
N-(5-chloro-2-hydroxy-phenyl)-3-[cycloheptyl(methyl)sulfamoyl]benzamide;
N-(3-aminopropyl)-3-[5-(5-chloro-2-hydroxy-phenyl)-1H-1,2,4-triazol-3-yl]-N-cyclohexyl-benzenesulfonamide;
N-(5-chloro-2-hydroxy-phenyl)-3-[cyclohexyl-[3-(dimethylamino)propyl]sulfamoyl]benzamide;
3-(5-chloro-1,3-benzoxazol-2-yl)-N-cyclohexyl-N-[3-(dimethylamino)propyl]benzenesulfonamide;
4-chloro-2-[4-[3-(1-piperidylsulfonyl)phenyl]triazol-1-yl]phenol;
4-chloro-2-[4-[3-(1-piperidylsulfonyl)phenyl]pyrimidin-2-yl]phenol;
N-(3-aminopropyl)-3-(1,3-benzothiazol-2-yl)-N-cyclohexyl-benzenesulfonamide;
3-[3-aminopropyl(cyclohexyl)sulfamoyl]-N-(2-methoxyphenyl)benzamide;
3-(1,3-benzoxazol-2-yl)-N-cyclohexyl-N-methyl-benzenesulfonamide;
3-[3-aminopropyl(cyclohexyl)sulfamoyl]-N-(2-hydroxyphenyl)benzamide;
N-(3-aminopropyl)-3-(1,3-benzoxazol-2-yl)-N-cyclohexyl-benzenesulfonamide;
3-[3-aminopropyl(cyclohexyl)sulfamoyl]-N-(2-hydroxy-3-methoxy-phenyl)benzamide;
N-(3-aminopropyl)-N-cyclohexyl-3-(7-methoxy-1,3-benzoxazol-2-yl)benzenesulfonamide;
N-(3-aminopropyl)-N-cyclohexyl-3-thiazolo[5,4-b]pyridin-2-yl-benzenesulfonamide;
2-[3-(1-piperidylsulfonyl)phenyl]benzotriazole;
N-(3-aminopropyl)-N-cyclohexyl-3-thiazolo[4,5-c]pyridin-2-yl-benzenesulfonamide;
N-(3-aminopropyl)-N-cyclohexyl-3-(7-hydroxy-1,3-benzoxazol-2-yl)benzenesulfonamide;
3-[3-aminopropyl(cyclohexyl)sulfamoyl]-N-(4,5-dichloro-2-hydroxy-phenyl)benzamide;
N-(3-aminopropyl)-N-cyclohexyl-3-(5,6-dichloro-1,3-benzoxazol-2-yl)benzenesulfonamide;
N-(3-aminopropyl)-3-(1H-benzimidazol-2-yl)-N-cyclohexyl-benzenesulfonamide;
N-(5-chloro-2-hydroxy-phenyl)-3-[cyclohexyl(3-morpholinopropyl)sulfamoyl]benzamide;
3-(5-chloro-1,3-benzoxazol-2-yl)-N-cyclohexyl-N-(3-morpholinopropyl)benzenesulfonamide;
3-(5-chloro-1,3-benzoxazol-2-yl)-N-cyclohexyl-N-(3-hydroxypropyl)benzenesulfonamide;
3-[5-(5-chloro-2-hydroxy-phenyl)-1H-1,2,4-triazol-3-yl]-N-cyclohexyl-N-methyl-benzenesulfonamide;
N-[5-chloro-2-hydroxy-4-(2-methoxyethoxy)phenyl]-3-(1-piperidylsulfonyl)benzamide;
N-(5-chloro-2-hydroxy-phenyl)-3-[cycloheptyl(methyl)sulfamoyl]benzamide;
ethyl 4-chloro-2-[[3-(1-piperidylsulfonyl)benzoyl]amino]benzoate;
N-(5-chloro-2-hydroxy-phenyl)-3-[(4-hydroxy-1-piperidyl)sulfonyl]benzamide;
4-chloro-2-[[3-(1-piperidylsulfonyl)benzoyl]amino]benzoic acid;
N-(3,5-dichloro-2-hydroxy-phenyl)-3-(1-piperidylsulfonyl)benzamide;
N-(5-chloro-1H-benzimidazol-2-yl)-3-(1-piperidylsulfonyl)benzamide;

N-(5-chloro-2-hydroxy-phenyl)-3-[(4,4-difluoro-1-piperidyl)sulfonyl]benzamide;

N-(3-acetyl-5-chloro-2-hydroxy-phenyl)-3-(1-piperidylsulfonyl)benzamide;

N-(5-chloro-2-hydroxy-3-methyl-phenyl)-3-(1-piperidylsulfonyl)benzamide;

N-[5-chloro-2-(1H-tetrazol-5-yl)phenyl]-3-(1-piperidylsulfonyl)benzamide;

N-[5-chloro-2-(N-hydroxycarbamimidoyl)phenyl]-3-(1-piperidylsulfonyl)benzamide;

N-(5-chloro-3-fluoro-2-hydroxy-phenyl)-3-(1-piperidylsulfonyl)benzamide; and

[4-chloro-2-[[3-(1-piperidylsulfonyl)benzoyl]amino]phenyl]dihydrogen phosphate.

6. A pharmaceutical composition comprising a compound of claim 3 and a pharmaceutically acceptable carrier.

7. The pharmaceutical composition according to claim 6 further comprising an additional active ingredient for the treatment of pain, respectively, wherein the active ingredients are administered simultaneously or sequentially.

8. An anti-pain pharmaceutical composition comprising a therapeutically effective amount of a compound according to claim 3.

9. A pharmaceutical composition comprising a compound of claim 4 and a pharmaceutically acceptable carrier.

10. The pharmaceutical composition according to claim 9 further comprising an additional anti-pain active ingredient, respectively, wherein the active ingredients are administered simultaneously or sequentially.

11. An anti-pain pharmaceutical composition comprising a therapeutically effective amount of a compound according to claim 4.

12. A pharmaceutical composition comprising a compound of claim 5 and a pharmaceutically acceptable carrier.

13. The pharmaceutical composition according to claim 12 further comprising an additional anti-pain active ingredient, respectively, wherein the active ingredients are administered simultaneously or sequentially.

14. An anti-pain pharmaceutical composition comprising a therapeutically effective amount of a compound according to claim 5.

15. A method of treating chronic pain or neuropathic pain comprising at least a step consisting in administering a compound according of formula (2) to claim 3 to a patient in need thereof.

16. A method of treating chronic pain or neuropathic pain comprising at least a step consisting in administering a compound according of formula (2a) to claim 4 to a patient in need thereof.

* * * * *